United States Patent [19]

Fobare et al.

[11] Patent Number: 5,281,714
[45] Date of Patent: Jan. 25, 1994

[54] N,N',N'-TRISUBSTITUTED-5-BISAMINOMETHYLENE-1,3-DIOXANE-4,6-DIONE INHIBITORS OF ACYL-COA: CHOLESTEROL-ACYL TRANSFERASE

[75] Inventors: William F. Fobare, Hamilton, N.J.; Donald P. Strike, St. Davids, Pa.

[73] Assignee: American Home Products Corporation, New York, N.Y.

[21] Appl. No.: 998,213

[22] Filed: Dec. 30, 1992

Related U.S. Application Data

[63] Continuation-in-part of Ser. No. 964,232, Oct. 21, 1992, abandoned, which is a continuation-in-part of Ser. No. 719,873, Jun. 24, 1991, Pat. No. 5,179,216, which is a continuation-in-part of Ser. No. 568,384, Aug. 16, 1990, abandoned.

[51] Int. Cl.$^5$ .......................... C07D 405/12
[52] U.S. Cl. ..................... 546/268; 546/159; 546/160; 546/171; 546/174; 548/194; 548/182; 548/183; 548/311.1; 548/304.7; 544/374; 544/148; 544/329
[58] Field of Search ........................ 546/268

[56] References Cited

U.S. PATENT DOCUMENTS 4,387,105 6/1983 DeVries et al. .................. 564/50
4,387,106 6/1983 DeVries et al. .................. 564/52

OTHER PUBLICATIONS

Augustin et al. CA 113: 231288t, 1990.
J. Med. Chem. 29, 1131 (1986), De Vries et al.
Stephen, Monat. Fur Chemie, 97, 45 (1966).
Derwent Abstract 40365K.

Primary Examiner—Jane T. Fan
Attorney, Agent, or Firm—Richard K. Jackson

[57] ABSTRACT

The compounds of the formula:

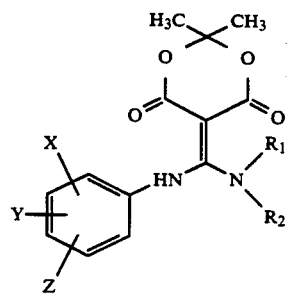

in which X, Y and Z are, independently, hydrogen, halogen, hydroxy, nitro, cyano, carboxyl, trifluoromethyl, phenyl, amino, alkylamino, dialkylamino, alkyl, alkoxy or phenylalkyloxy; $R_1$ is thienyl, imidazolyl, thiazolyl, pyridinyl, quinolinyl, pyrimidinyl, pyrazinyl, benzamidazolyl, phenylalkylpiperidinyl or morpholino or athaae analogous hetercyclic groups with from one to tahree substituents selected from halogen, hydroxy, nitro, cyano, carboxyl, trifluoromethyl, phenyl, amino, alkylamino of 1 to 6 carbon atoms, dialkylamino in which each alkyl group has 1 to 6 carbon atoms, alkyl of 1 to 6 carbon atoms, or alkoxy of 1 to 6 carbon atoms; $R_2$ is hydrogen, alkyl, cycloalkyl, phenyl, benzyl or substituted phenyl or benzyl in which said substituent is alkyl, alkoxy, halogen, cyano, trifluoromethyl amino, nitro, alkylamino or dialkylamino; and a pharmaceutically acceptable salt thereof; are ACAT inhibitors, some of which possess antioxidant properties.

6 Claims, No Drawings

N,N',N'-TRISUBSTITUTED-5-BISAMINOMETHYLENE-1,3-DIOXANE-4,6-DIONE INHIBITORS OF ACYL-COA: CHOLESTEROL-ACYL TRANSFERASE

RELATED APPLICATION

This application is a continuation-in-part of copending U.S. patent application Ser. No. 07/964,232, filed Oct. 21, 1992, now abandoned which is a continuation-in-part of copending Ser. No. 07/719,873, filed Jun. 24, 1991, U.S. Pat. No. 5,179,216 issued Jan. 12, 1993 which in turn is a continuation-in-part of copending U.S. patent application Ser. No. 07/568,384, filed Aug. 16, 1990, now abandoned.

BACKGROUND OF THE INVENTION

This invention relates to chemical compounds which display inhibition of Acyl-Coenzyme A: Cholesterol Acyltransferase (ACAT). Compounds of this type aid in reducing cholesterol absorption and its effect on atherosclerosis.

Atherosclerosis is the most common form of arteriosclerosis and is characterized by the buildup of phospholipids and esterified cholesterol in large and medium arteries causing them to be inelastic and thus weakened. These inelastic and occluded arteries are the most common cause of ischemic heart disease.

ACAT is an important enzyme for the intracellular esterification of cholesterol. Studies of this enzyme in cultured cells (M. S. Brown, J. Biol. Chem. 255(19),pp.9344-9352 (1980)) has shown that increases in ACAT activity represent increases in the presence of cholesterol laden lipoproteins. Regulation of ACAT helps prevent the absorption of cholesterol in the intestinal mucosa and assists in the reversal of already present atherosclerotic lesions.

DESCRIPTION OF THE INVENTION

In accordance with this invention, there is provided a group of diaminomethylene dioxane dione derivatives of the formula:

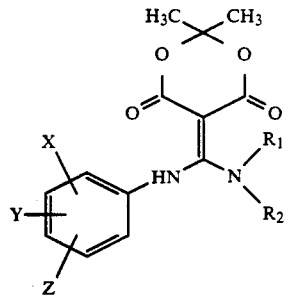

in which
X, Y and Z are, independently, hydrogen, halogen, hydroxy, nitro, cyano, carboxyl, trifluoromethyl, phenyl, amino, alkylamino of 1 to 6 carbon atoms, dialkylamino in which each alkyl group has 1 to 6 carbon atoms, alkyl of 1 to 6 carbon atoms, alkoxy of 1 to 6 carbon atoms or phenylalkyloxy of 7 to 9 carbon atoms;

$R_1$ is alkyl of 1 to 18 carbon atoms, hydroxyalkyl of 1 to 18 carbon atoms, alkenyl of 1 to 18 carbon atoms, cycloalkyl of 5 to 8 carbon atoms, phenylcycloalkyl in which the cycloalkyl moiety has 5 to 8 carbon atoms, 1-hydroxymethylphenethyl, 1-(t-butyl)dimethylsilyloxymethylphenethyl, 1-(t-butyl)dimethylsilyoxymethylisopentyl, 1-hydroxymethylisopentyl, phenyl, benzyl or substituted phenyl or benzyl where the substituents are alkyl of 1 to 12 carbon atoms, alkoxy of 1 to 12 carbon atoms, halogen, cyano, trifluoromethyl, amino, alkylamino of 1 to 6 carbon atoms, dialkylamino in which each alkyl group has 1 to 6 carbon atoms, nitro or phenyl, benzyl, phenethyl or $R_1$ is thienyl, imidazolyl, thiazolyl, pyridinyl, pyrimidinyl, pyrazinyl, benzamidazolyl, phenylalkylpiperidinyl in which the alkyl moiety has from 1 to 6 carbon atoms or morpholino, in which the heterocyclic moieties can be substituted with one to three substituents selected from halogen, hydroxy, nitro, cyano, carboxyl, trifluoromethyl, phenyl, amino, alkylamino of 1 to 6 carbon atoms, dialkylamino in which each alkyl group has 1 to 6 carbon atoms, alkyl of 1 to 6 carbon atoms, or alkoxy of 1 to 6 carbon atoms;

$R_2$ is alkyl of 1 to 18 carbon atoms, cycloalkyl of 5 to 8 carbon atoms, phenyl, benzyl or substituted phenyl or benzyl in which said substituent is alkyl of 1 to 6 carbon atoms, alkoxy of 1 to 6 carbon atoms, halogen, cyano, trifluoromethyl amino, nitro, alkylamino of 1 to 6 carbon atoms or dialkylamino of 1 to 6 carbon atoms and when $R_1$ is a heterocyclic group, $R_2$ may be hydrogen;

or a pharmaceutically acceptable salt thereof.

The halogen substituent referred to above may be chlorine, bromine, fluorine or iodine, fluorine being preferred. The pharmaceutically acceptable salts are derived from known inorganic or organic acids such as hydrochloric, hydrobromic, sulfuric, nitric, phosphoric, methanesulfonic, ethanesulfonic, hydroxyethanesulfonic, toluene sulfonic, naphthalenesulfonic, formic, acetic, propionic, oxalic, succinic, glycollic, lactic, malic, tartaric, citric, ascorbic, maleic, hydroxymaleic, pyruvic, phenylacetic, benzoic, para-amino benzoic, para-hydroxybenzoic, salicylic, sulfanilic acids, and the like.

Of these compounds, those preferred on the basis of their in vitro and in vivo potency are:

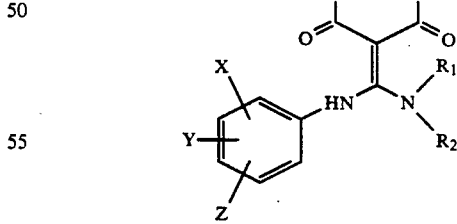

in which
X, Y and Z are, independently, alkyl of 1 to 6 carbon atoms, alkoxy of 1 to 6 carbon atoms, hydroxy, dialkylamino in which each alkyl group has from 1 to 6 carbon atoms or aralkoxy of 7 to 10 carbon atoms;

$R_1$ is alkyl of 1 to 18 carbon atoms, 1-(t-butyl)dimethyl-silyloxymethylphenethyl, 1-(t-butyl)dimethyl-silyloxymethylisopentyl, phenylcycloalkyl in which the cycloalkyl group has 5 to 8 carbon atoms or hydroxy alkyl of 1 to 18 carbon atoms; and $R_2$ is alkyl- or alkoxy-substituted benzyl, in which the alkyl and alkoxy substituents contain 1 to 6 carbon atoms;

or a pharmaceutically acceptable salt thereof.

Of the N-heterocylic derivatives of this invention, the preferred compounds are those of the formula:

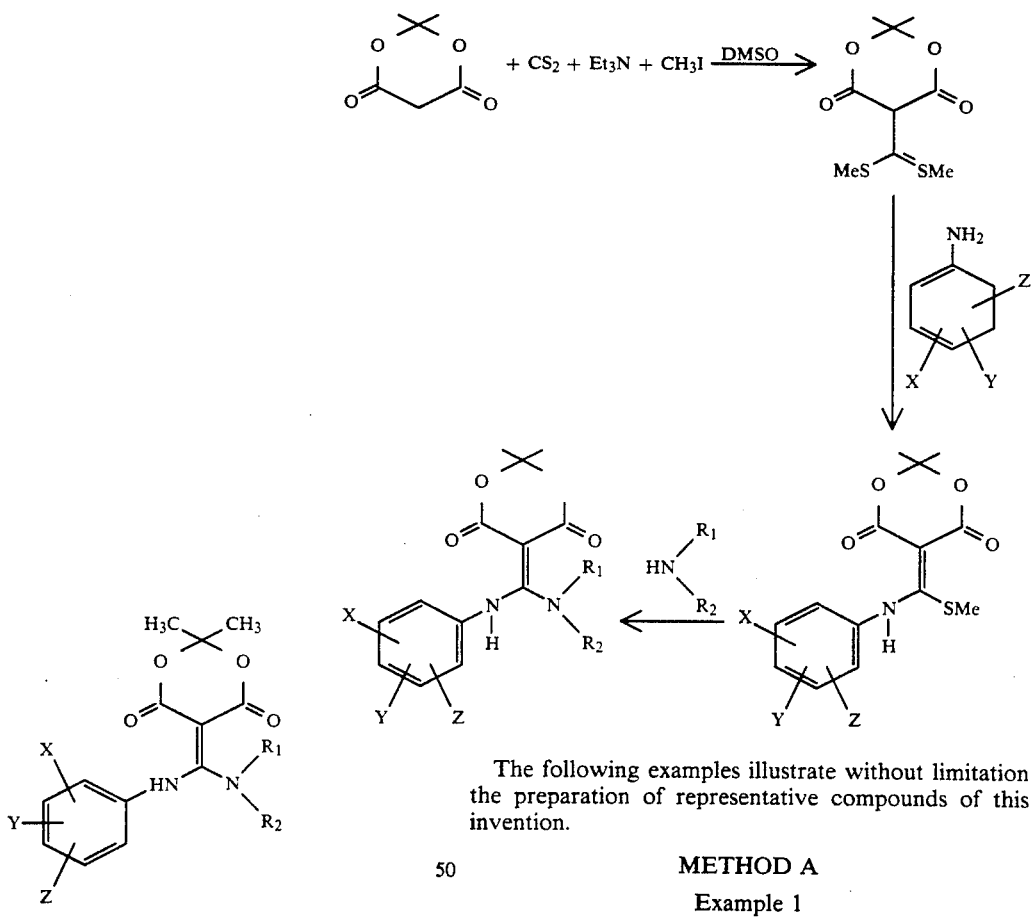

in which

X, Y and Z are, independently, alkyl of 1 to 6 carbon atoms, alkoxy of 1 to 6 carbon atoms, hydroxy, dialkylamino in which each alkyl group has from 1 to 6 carbon atoms or aralkoxy of 7 to 10 carbon atoms;

$R_1$ is quinolinyl, pyridinyl, piperidinyl or phenylalkylpiperidinyl in which the alkyl group contains 1 to 6 carbon atoms and each of the heterocyclic moieties can be substituted by from one to three substituents selected from halogen, hydroxy, nitro, cyano, carboxyl, trifluoromethyl, phenyl, amino, alkylamino of 1 to 6 carbon atoms, dialkylamino in which each alkyl group has 1 to 6 carbon atoms, alkyl of 1 to 6 carbon atoms, or alkoxy of 1 to 6 carbon atoms; and $R_2$ is hydrogen, alkyl of 1 to 18 carbon atoms, cycloalkyl of 5 to 8 carbon atoms, phenyl, benzyl or substituted phenyl or benzyl in which said substituent is alkyl of 1 to 6 carbon atoms, alkoxy of 1 to 6 carbon atoms, halogen, cyano, trifluoromethyl amino, nitro, alkylamino of 1 to 6 carbon atoms or dialkylamino of 1 to 6 carbon atoms;

or a pharmaceutically acceptable salt thereof.

The compounds of this invention are prepared by conversion of 2,2-dimethyl-1,3-dioxane-4,6-dione to the corresponding 5-bis (methylthio) methylene derivative with carbon disulfide and methyl iodide in dimethylsulfoxide in the presence of a base such as triethylamine, followed by sequential displacement of the methylthio groups with the desired amines, thusly:

The following examples illustrate without limitation the preparation of representative compounds of this invention.

METHOD A

Example 1

5-[(Dihexylamino)[(2,4-dimethoxyphenyl)amino]methylene]-2,2-dimethyl-1,3-dioxane-4,6-dione Procedure 1

To a solution containing 2.0 g (8.05 mmol) of 5-[bis(-methylthio)methylene]-2,2-dimethyl-1,3-dioxane-4,6-dione 1 in 40 mL of t-butanol, was added 1.23 g (8.05 mmol) of 2,4-dimethoxy aniline. The reaction mixture was allowed to stir at reflux for 24 hours. The mixture was cooled to room temperature and diluted with hexanes. The solid was filtered and used without further purification. Isolated: 2.3 g, 81% yield.

Procedure 2

To a solution of 0.6 g (1.7 mmol) of 5-[[(2,4-dimethoxyphenyl)amino]methylthiomethylene]-2,2-dimethyl-1,3-dioxane-4,6-dione in 22 mL of 50:50 t-butanolacetonitrile was added 0.395 mL (1.7 mmol) of N-dihexylamine, 0.27 g (0.9 mmol) of mercuric sulfate and 0.23 mL (1.7 mmol) of trimethylamine. The reaction mixture was refluxed for 4 h, then cooled to room temperature. Dilution with 50:50 hexanes-ethyl acetate and filtration through celite followed by removal of solvents under reduced pressure yielded an oil. Column Chromatography on silica gel (1:1 ethyl acetate-hexanes) yielded 0.72 g (87%) of a solid, m.p. 156°-157.5° C. TLC (1:1 ethyl acetate-hexane) $R_f$=0.09; IR (KBr) 2830, 1696, 1645, 1512, 1208, 940 cm$^{-1}$. $^1$H NMR (400 MHz, CDCl$_3$) δ 8.33 (s, 1H, exchangeable), 7.06 (d, 1H, J=8.7 Hz), 6.49 (d, 1H, J=2.6 Hz), 6.44 (dd, 1H, J=2.6, 8.7 Hz), 3.82 (s, 3H), 3.80 (s, 3H), 3.21 (m, 4H), 1.64 (s, 6H), 1.59 (s, 4H), 1.27 (m, 12H), 0.87 (t, 6H, J=6.7 Hz).

Elemental analysis for: $C_{27}H_{42}N_2O_6$: Calc'd: C, 66.10; H, 8.63; N, 5.71; Found: C, 66.09; H, 8.46; N, 5.70.

METHOD B

Example 2

5-[[(2,4-Dimethoxyphenyl)amino][[[4-(1,1-dimethylethyl)phenyl]methyl]heptylamino]methylene]-2,2-dimethyl-1,3-dioxane-4,6-dione Procedure 1

To a solution of 37 mL (0.25 mol) 1-heptylamine, 36 mL (0.26 mol) of triethylamine in 300 mL of CHCl$_3$ was added 49.6 mL (0.25 mol) of 4-t-butyl benzoyl chloride dropwise. The reaction mixture was stirred at room temperature for 20 h then poured into H$_2$O. The layers were separated and the organic layer washed twice with H$_2$O. The CHCl$_3$ layer was dried (MgSO$_4$) and the solvent removed at reduced pressure. The impure compound was used without further purification.

Procedure 2

To a solution of 68.8 g (0.25 mol) of the amide from procedure 1 in 400 mL of dry toluene was added 105 mL of 70% Red-Al in toluene, dropwise. The reaction mixture stirred at room temperature for 0.5 h then at reflux for 15 h. The solution was cooled, quenched with saturated NH$_4$Cl and the solvent removed under reduced pressure. The residue was taken up in aqueous HCl and the ammonium salt extracted with CHCl$_3$ three times. The combined organic layers were dried (MgSO$_4$) and the solvent removed at reduced pressure. The salt was then crystallized from ether, filtered and washed with ether. The ammonium salt was than basified with aqueous NaOH and extracted three times with Et$_2$O which was dried (Na$_2$SO$_4$) and the solvent removed at reduced pressure. This amine was used as is without further purification.

Procedure 3

To a solution of 0.6 g (1.7 mmol) 3-[[(2,4-dimethoxyphenyl)amino]methylthiomethylene]-2,2-dimethyl-1,3-dioxane-4,6-dione (Method A, procedure 1) in 20 mL of 50:50 acetonitrile/t-butanol was added 0.44 g (1.7 mmol) of N-4-t-butylbenzyl-N-heptylamine (Procedure 2), 0.27 g (0.8 mmol) of mercuric sulfate and 0.23 mL (1.7 mmol) of triethylamine. The solution was refluxed for 4 h and cooled to room temperature. The solution was diluted with ethyl acetate and filtered through celite. The solvents were removed under reduced pressure and chromatography on silica gel (1:1 hexanes-ethyl acetate) yielded 0.81 g (85%) of a white solid (m.p. 100°-103° C.) homogeneous by TLC and spectroscopic considerations. TLC (1:1 hexanes-ethyl acetate) $R_f$ 0.23; IR (KBr) 2950, 1700, 1630, 1512, 1208, 1035, 931 cm$^{-1}$. $^1$H NMR (400 MHz, CDCl$_3$) δ 7.36 (d, 2H, J=8.3 Hz), 7.23 (d, 2H, J=8.3 Hz), 7.02 (d, 1H, J=8.7 Hz), 6.46 (d, 1H, J=2.6 Hz), 6.37 (dd, 1H, J=2.6, 8.7 Hz), 4.40 (br s, 2H), 3.78 (s, 3H), 3.77 (s, 3H), 3.13 (m, 2H), 1.63 (s, 6H), 1.31 (s, 9H), 1.17 (br s, 10H), 0.84 (t, 3H, J=6.8 Hz).

Elemental analysis for: $C_{33}H_{46}N_2O_6$: Calc'd: C, 69.94; H, 8.18; N, 4.94; Found: C, 69.81; H, 8.20; N, 4.95.

METHOD C

Example 3

5-[(Dihexylamino)[(4-fluorophenyl)amino]methylene]-2,2-dimethyl-1,3-dioxane-4,6-dione Procedure 1

To a solution of 2.0 g (8.05 mmol) of 5-[bis(methylthio)methylene]-2,2-dimethyl-1,3-dioxane-4,6-dione 1 in 30 mL of t-butanol was added 0.76 mL (8.05 mmol) of 4-fluoroaniline. The reaction mixture was allowed to stir at reflux for 48 h. The mixture was cooled to room temperature and filtered. 1.97 g (79%) of a yellow solid was isolated and used without further purification or characterization.

Procedure 2

To a solution containing 0.6 g (1.9 mmol) of 3-[[(4-fluorophenyl)amino]methylthio-methylene]-2,2-dimethyl-1,3-dioxane-4,6-dione in 16 mL of 50:50 acetonitrile-t-butanol was added 0.44 mL (1.9 mmol) of dihexylamine, 0.31 g (1 mmol) of mercuric sulfate and 0.27 mL (1.9 mmol) of triethylamine. The solution was stirred at reflux for 4 h. The reaction mixture was cooled to room temperature, diluted with ethyl acetate and filtered through celite. The solvents were removed at reduced pressure and column chromatography of the residue on silica gel (1:1 ethyl acetate-hexanes) yielded 0.60 g (70%) of a white solid (m.p. 145°-147° C.) homogeneous by spectroscopic criteria. TLC (1:1 ethyl acetate-hexanes) $R_f$ 0.17; IR (KBr) 2968, 2940, 2870, 1699, 1645, 1513, 1345, 1220, 1082, 839 cm$^{-1}$. $^1$H NMR (400 MHz, CDCl$_3$) δ 9.08 (br s, 1H, exchangeable), 7.08 (m, 4H), 3.16 (t, 4H, J=7.2 Hz), 1.64 (s, 6H), 1.57 (m, 4H), 1.24 (br s, 12H), 0.85 (t, 6H, J=6.8 Hz).

Elemental analysis for: $C_{25}H_{37}FN_2O_4$: Calc'd: C, 66.96; H, 8.26; N, 6.25; Found: C, 66.80; H, 8.15; N, 6.15.

METHOD D

Example 4

5-[[(2,4-Dimethoxyphenyl)amino][[[4-(1,1-dimethylethyl)phenyl]methyl](1-methylhexyl)amino]methylene]-2,2-dimethyl-1,3-dioxane-4,6-dione Procedure 1

The N-t-butylbenzyl-N-(1-methylhexyl)amine was synthesized in the same manner as in Example 2, procedures 1 and 2 using 4-t-butylbenzoyl chloride and 2-aminoheptane as starting materials.

Procedure 2

To a solution of 0.62 g (1.75 mmol) of [[(2,4-dimethoxyphenyl)amino]methylthiomethylene]-2,2-dimethyl-1,3-dioxane-4,6-dione (Method A, Procedure 1) in 6 mL of 50:50 acetonitrile-t-butanol was added 0.46 g (1.75 mmol) of N-4-(2,2-dimethylethyl)benzyl-N-heptylamine[synthesized as in Example 2, Procedure 2 from 2-aminoheptane and 4-(2,2-dimethylethyl)benzoyl chloride], 0.31 g (1.05 mmol) mercuric sulfate and 0.25 mL (1.75 mmol) of triethylamine. The reaction mixture stirred at reflux for 18 h. The solution was cooled to room temperature, diluted with ethyl acetate, filtered through celite and the solvents were removed at reduced pressure. Column chromatography of the residue on silica gel (2:1 hexane-ethyl acetate) yielded 0.87 g (75%) of a light yellow solid (m.p. 86°–89° C.) homogeneous by spectroscopic criteria. $R_f$ (1:1 hexanes-ethyl acetate) 0.21; IR (KBr) 2960, 1635, 1565, 1515, 1465, 1210, 1160, 935 cm$^{-1}$. $^1$H NMR (400 MHz, CDCl$_3$) δ 7.39 (d, 2H, J=7.89 Hz), 7.32 (br m, 2H), 7.12 (d, 2H, J=9.28), 6.36 (m, 3H), 4.64 (br s, 2H), 4.30 (br m, 1H), 3.75 (s, 3H), 3.67 (s, 3H), 1.78 (br m, 2H), 1.58–1.25 (m, 18H), 0.86 (t, 3H, J=6.8 Hz).

Elemental analysis for: $C_{33}H_{46}N_2O_6$: Calc'd: C, 69.94; H, 8.18; N, 4.94; Found: C, 69.01; H, 8.03; N, 4.77.

METHOD E

Example 5

5-[[[4-(Dimethylamino)phenyl]amino][[[4-(1,1-dimethylethyl)phenyl]methyl]heptylamino]-methylene]-2,2-dimethyl-1,3-dioxane-4,6-dione Procedure 1

To a solution of 0.74 g (3.0 mmol) of 5-[bis(methylthio)methylene]-2,2-dimethyl-1,3-dioxane-4,6-dione 1 in 10 mL of acetonitrile was added 0.41 g (3.0 mmol) of N,N-dimethyl-1,4-phenylenediamine. The reaction mixture was allowed to reflux for 18 h. After cooling to room temperature, the solvents were removed at reduced pressure and the residue was recrystallized from ethyl acetate-hexanes to yield 0.773 g (77%) of a dark green powder which was used without further characterization.

Procedure 2

To a solution of 0.59 g (1.75 mmol) of [[(2,4-dimethylphenyl)amino]methylthiomethylene]-2,2-dimethyl-1,3-dioxane-4,6-dione (Method E, Procedure 1) in 6 mL of 50:50 acetonitrile-hexanes was added 0.46 g (1.75 mmol) of N-4-(dimethylethyl)-benzyl-N-heptylamine, 0.31 g (1.75 mmol) of mercuric sulfate and 0.25 mL of triethylamine. The reaction mixture was allowed to stir at reflux for 18 h then was cooled to room temperature. The mixture was diluted with ethyl acetate and filtered through celite. The solvent was removed at reduced pressure and the residue chromatographed on silica gel (1:2 hexanes-ethyl acetate to 1:9 hexanes-ethyl acetate) to yield 0.84 g (88%) of a yellow solid (m.p. 103°–106° C.) homogeneous by spectral considerations. $R_f$ 0.12 (1:1 ethylacetate-hexanes); IR (KBr): 2950, 1622, 1515, 1348, 1196 1078, 920 cm$^{-1}$; $^1$H NMR (400 MHz, CDCl$_3$) δ 7.37 (d, 2H, J=8.3H), 7.24 (d, 2H, J=8.3 Hz), 6.96 (d, 2H, J=8.8 Hz), 6.60 (d, 2H, J=8.8 Hz), 4.39 (br s, 2H), 3.09 (br m, 2H), 2.93 (s, 6H), 1.63 (s, 6H), 1.31 (s, 9H), 1.25-1.15 (m, 10H), 0.85 (t, 3H, J=6.8 Hz).

Elemental analysis for: $C_{33}H_{47}N_3O_4$: Calc'd: C, 72.10; H, 8.62; N, 7.64; Found: C, 72.21; H, 8.63; N, 7.77.

METHOD F

Example 6

5-[[(-2,4-Dimethoxyphenyl)amino][heptyl[[4-[(3-methylbutyl)oxy]phenyl]methyl]amino]-methylene]-2,2-dimethyl-1,3-dioxane-4,6-dione Procedure 1

To a solution of 30 g (0.18 mol) of ethyl-4-hydroxybenzoate in 200 mL of DMSO was added 24.9 g of anydrous K$_2$CO$_3$ and 21.6 mL (0.18 mol) of 1-bromo-3-methyl butane. The reaction mixture was allowed to stir at room temperature for 1 h then at 70° C. for 14 h. The mixture was poured into ethyl acetate and washed 4 times with H$_2$O, then the organic layer was dried (MgSO$_4$) and the solvents removed at reduced pressure. The residue was used without further purification or characterization.

Procedure 2

The ester (Method F, procedure 1) was dissolved in 200 mL of ethanol and 8.8 g (0.22 mol) of NaOH in 70 mL of H$_2$O was added. The reaction mixture stirred at room temperature for 19 h. The ethanol was removed at reduced pressure and the residue added to 300 mL of H$_2$O. The aqueous layer was washed twice with ethyl ether and the aqueous layer acidified with conc. HCl. The aqueous layer was then extracted 3 times with ethyl acetate and the ethyl acetate layers were combined, dried (MgSO$_4$) and the solvent removed at reduced pressure. The residue was used as is without further purification or characterization.

Procedure 3

The acid prepared in Method F, procedure 2, was dissolved in 200 mL of CHCl$_3$ and 23.3 mL (0.26 mol) oxalyl chloride was added at 0° C. over 0.5 h period. After 0.5 h at 0° C. the reaction mixture was warmed to room temperature for 24 h. The solvents were then removed at reduced pressure and vacuum distillation (0.2 mm Hg) yielded 33 g of an oil (b.p. 120°–122° C.) which was used as is without further characterization of purification.

Procedure 4

To a solution of 10.6 mL (72 mmol) of 1-aminoheptane in 300 mL of CH$_2$Cl$_2$ and 10.0 mL (72 mmol) of Et$_3$N at 0° C., was added 15 g (66 mmol) of 4-[4-methylpentyl)oxy]-benzoyl chloride. The reaction mixture stirred at 0° C. for 0.25 h then to room temperature for 16 h. The reaction mixture was poured into CH$_2$Cl$_2$ and washed 3 times with H$_2$O. The organic layer was dried (MgSO$_4$) and the solvents were removed at reduced pressure. This was used without further characterization or purification.

Procedure 5

To a solution of 19.8 g (65 mmol) of the amide from Method F, procedure 4 in 400 mL of toluene was added at 0° C., 47.7 mL (0.162 mol) of Red-Al over a 10 minute period. The solution was then refluxed for 6 h and upon cooling, quenched with sat'd NH$_4$Cl and the toluene was removed at reduced pressure. To this residue was added 3N HCl to pH 2. The residue was extracted 3 times with CHCl$_3$ and the combined CHCl$_3$ layers were dried (MgSO$_4$) and the solvent removed at reduced pressure. The hydrochloride salt was washed with ethyl ether and filtered. The hydrochloride salt was then basified with aqueous NaOH and extracted 3 times with ethyl ether. The ether was dried (Na$_2$SO$_4$) and the solvents were removed at reduced pressure. The amine was used without further purification or characterization.

Procedure 6

To a solution of 0.78 g (2.2 mmol) of 5-[(2,4-dimethoxyphenyl)amino]-5-methylthio-methylene-2,2-dimethyl-1,3 dioxane-4,6-dione in 8 mL of 50:50 acetonitrile-t-butanol was added 0.67 g (2.3 mmol) of N-[(4-methylpentyl)oxy]phenyl]methyl-N-heptylamine, 0.38 g (1.32 mmol) of mercuric sulfate and 0.31 mL (2.2 mmol) of Et$_3$N. The reaction mixture was allowed to stir at reflux for 18 h. The mixture was cooled to room temperature, diluted with ethyl acetate and filtered through celite. The solvents were removed at reduced pressure and column chromatography of the residue on silica gel (1:1 ethyl acetate-hexanes then 4:1 ethyl acetate-hexanes) yielded 1.25 g (95%) of a pale yellow solid (m.p. 67°–70° C.). $R_f$ 0.12 (1:1 ethyl acetate-hexanes); IR (KBr) 2940, 2888, 1710, 1640, 1522, 1215, 1042, 938 cm$^{-1}$; $^1$H NMR (400 MHz, CDCl$_3$) δ 7.22 (d, 2H, J=8.6 Hz), 7.03 (d, 1H, J=8.7 Hz), 6.86 (d, 2H, J=8.6 Hz), 6.46 (d, 1H, J=2.6 Hz), 6.38 (m, 1H), 4.34 (br s, 2H), 3.98 (t, 2H, J=6.7 Hz), 3.79 (s, 3H), 3.78 (s, 3H), 3.08 (m, 2H), 1.83 (m, 1H), 1.70–1.65 (m, 8H), 1.30–1.16 (m, 10H), 0.96 (d, 6H, J=6.6 Hz), 0.85 (t, 3H, J=7.1 Hz).

Elemental analysis for: C$_{34}$H$_{48}$N$_2$O$_7$; Calc'd: C, 68.43; H, 8.11; N, 4.69; Found: C, 68.42; H, 8.36; N, 4.67.

METHOD G

Example 7

5-[[(2,4-Dimethoxyphenyl)amino][[[4-(2,2-dimethylpropyl)phenyl]methyl](1-methylhexyl)amino]methylene]-2,2-dimethyl-1,3-dioxane-4,6-dione Procedure 1

The N-4-[(2,2-dimethylpropyl)phenyl]methyl-N-1-methylhexyl amine was synthesized as in *J. Med. chem.* 1986, 29, 1131, using 2-aminoheptane and 4-neopentylbenzene as starting materials.

Procedure 2

To a solution of 0.71 g (2.0 mmol) of 5-[(2,4-dimethoxyphenyl)amino]-5-methylthiomethylene-2,2-dimethyl-1,3 dioxane-4,6-dione in 6 mL of 50:50 acetonitrile-t-butanol was added 0.55 g (2.0 mmol) of the N-4-neopentylbenzyl-N-2-heptylamine (Method 6, procedure 1), 0.35 g (1.2 mmol) mercuric sulfate and 0.28 mL (2.0 mmol) of Et$_3$N. The reaction mixture was allowed to reflux for 18 h then cooled to room temperature. The solution was diluted with ethyl acetate, filtered through celite and the solvents removed under reduced pressure. Column chromatography of the residue on silica gel (1:1 ethyl acetate-hexanes to 4:1 ethyl acetate-hexanes) yielded after recrystallization (ethyl acetate-hexanes) 1.02 g (88%) of a white solid (m.p. 157°–158° C.) homogeneous by spectral considerations. TLC (1:1 ethyl acetate-hexanes) R$_f$0.07; IR (KBr) 2960, 1703, 1640, 1569, 1516, 1211, 938 cm$^{-1}$; $^1$H NMR (400 MHz, CDCl$_3$) δ 7.30 (m, 2H), 7.21 (m, 3H), 6.34 (m, 2H), 4.64 (br s, 2H), 4.25 (br m, 1H), 3.66 (s, 3H), 3.64 (s, 3H), 2.45 (s, 2H), 1.76–1.19 (br m, 17H), 0.86 (br s, 12H).

Elemental analysis for: C$_{34}$H$_{48}$N$_2$O$_6$; Calc'd: C, 70.32; H, 8.33; N, 4.82; Found: C, 70.34; H, 8.37; N, 4.79.

METHOD H

Example 8

5-[[(2,4-Dimethoxyphenyl)amino][[[4-(2-methylpropyl)phenyl]methyl][1-(phenylmethyl)-4-piperidinyl]amino]methylene]-2,2-dimethyl-1,3-dioxane-4,6-dione Procedure 1

The N-(4-isobutylbenzyl)-N-4-(N'-benzylpiperidinyl) amine was synthesized as in Method 6, procedure 1 using 4-amino-N-benzylpiperidine and isobutyl benzene as starting materials.

Procedure 2

To a solution of 0.71 g (2.0 mmol) of 5-[(2,4-dimethoxyphenyl)amino]-5-methylthiomethylene-2,2-dimethyl-1,3-dioxane-4,6-dione in 20 mL of acetonitrile was added 0.67 g (2.0 mmol) N-(4-isobutylbenzyl)-N-4-(N'-benzylpiperidinyl) amine, 0.35 g (1.2 mmol) HgSO$_4$ and 0.28 mL (21.0 mmol) of Et$_3$N. The reaction mixture was allowed to reflux for 18 h, then it was cooled to room temperature, diluted with ethyl acetate and filtered through celite. The solvents were removed at reduced pressure and a column chromatography of the residue on silica gel (10% MeOH-ethyl acetate) yielded 0.73 g of a solid (m.p. 115°–118° C.); IR (KBr) 3410, 3212, 2935, 1692, 1622, 1558, 1504, 1455, 1372, 1328, 1300, 1245, 1198, 1148, 1071, 1018, 990, 915, 819, 773, 718 cm$^{-1}$; $^1$H NMR (400 MHz, CDCl$_3$) δ 7.31–7.21 (m, 7H), 7.14 (d, 2H, J=7.64 Hz), 7.07 (d, 1H, J=8.4 Hz), 6.34 (d, 2H, J=8.64 Hz), 4.72 (br m, 2H), 4.18 (br m, 1H), 3.73 (s, 3H), 3.65 (s, 3H), 3.43 (s, 2H), 2.87 (br d, 2H, J=10.28 Hz), 2.45 (d, 2H, J=7.2 Hz), 1.98–1.30 (br m, 14H), 0.87 (d, 6H, J=6.56 Hz).

Elemental analysis for: C$_{38}$H$_{47}$N$_3$O$_6$: Calc'd: C, 71.11; H, 7.38; N, 6.55; Found: C, 70.80; H, 7.67; N, 6.54.

METHOD I

Example 9

5-[[(2,4-Dimethoxyphenyl)amino][[(1-phenylcyclopentyl)methyl]amino]methylene]-2,2-dimethyl-1,3-dioxane-4,6-dione Procedure 1

To a solution of 25 g (0.14 mol) of 1-cyano-1-phenylcyclopentane in 400 mL of toluene at 0° C. was added 107 mL (0.36 mol) of 3.4M Red-Al over a 20 minute period. The reaction mixture was allowed to stir for an additional 23 h at room temperature when it was quenched with sat'd NH$_4$Cl and the solvent removed at reduced pressure. The residue was added to aqueous acid and extracted four times with CHCl$_3$, which were combined, dried (MgSO$_4$) and the solvent removed at reduced pressure. The hydrochloride salt was triturated with ethyl ether and then added to aqueous NaOH and extracted 3 times with ether. The combined ether layers were dried (Na$_2$SO$_4$) and the solvent removed at reduced pressure. The oil was used as is without further purification or characterization.

Procedure 2

To a solution of 0.44 g (2.5 mmol) of 1-aminomethyl-1-phenylcyclopentane in 20 mL of 1:1 t-butanol-acetonitrile was added 0.88 g (2.5 mmol) of 5-[(2,4-dimethoxyphenyl)amino]-5-methylthiomethylene-2,2-dimethyl-1,3-dioxane-4,6-dione and 0.35 mL (2.5 mmol) of Et$_3$N. The mixture was allowed to reflux for 4 days then stir at room temperature for 3 days. The solvents were removed at reduced pressure and chromatography on silica gel (2:1 hexanes-ethyl acetate) yielded a solid (m.p. 49°–52° C.); IR (KBr) 3440, 2962, 2880, 1660, 1413, 1465, 1395, 1348, 1312, 1265, 1210, 1172, 1111, 1029, 923, 798, 765, 701 cm$^{-1}$; $^1$H NMR (400 MHz, CDCl$_3$) δ 10.90 (br s, 1H), 9.82 (br s, 1H), 7.33–7.18 (m, 5H), 6.93 (d, 1H, J=8.44 Hz), 6.48 (d, 1H, J=2.56 Hz), 6.45 (dd, 1H, J=8.52, 2.64 Hz), 3.85 (s, 3H), 3.78 (s, 3H), 2.88 (d, 2H, J=4.88 Hz), 1.90–1.51 (m, 14H).

Elemental analysis for: C$_{27}$H$_{32}$N$_2$O$_6$: Calc'd: C, 67.48; H, 6.71; N, 5.83; Found: C, 67.19; H, 6.64; N, 5.62.

METHOD J

Example 10

5-[[(2,4-Dimethoxyphenyl)amino][[[4-(2,2-dimethylpropyl)phenyl]methyl][(1-phenylcyclo-pentyl)methyl]amino]methylene]-2,2-dimethyl-1,3-dioxane-4,6-dione Procedure 1

To a solution of 7.0 g (40.0 mmol) of 1-aminomethyl-1-phenyl cyclopentane (Method I, Procedure 1) 11.2 mL (80.0 mmol) of Et$_3$N and 125 mL of CHCl$_3$ at 0° C. was added 8.4 g (40.0 mmol) of 4-neopentylbenzoyl chloride. After addition the flask was warmed to room temperature and the mixture was stirred for 2 h. The mixture was poured into CHCl₃ and washed 3 times with H₂O then dried (MgSO₄)) and the solvents removed at reduced pressure. The oil obtained was dissolved in 150 mL of toluene at 0° C. and 29.4 mL (100 mmol) of 3.4M Red-Al was added dropwise over 15 min. then the reaction mixture was heated to reflux for 3 h and cooled to 0° C. where the reaction was carefully quenched with sat'd NH₄Cl. The toluene was removed at reduced pressure and the residue was acidified to pH2. The aqueous solution was extracted 3 times with CHCl₃ which was dried (MgSO₄) and the solvent was removed at reduced pressure. The salt was added to aqueous base and extracted with CHCl₃ which was dried (Na₂SO₄) and solvent removed at reduced pressure. The oil obtained was used without further purification of characterization.

Procedure 2

To a solution of 1.24 g (3.5 mmol) of 5-[(2,4-dimethoxyphenyl)amino]-5-methylthiomethylene-2,2-dimethyl-1,3-dioxane-4,6-dione, 0.61 g (2.1 mmol) HgSO₄ and 0.49 mL (3.5 mmol) of Et₃N in 40 mL of 1:2 t-butanol-acetonitrile was added 1.17 g (3.5 mmol) of the amine from Method J, procedure 1. The reaction mixture was allowed to stir at reflux for 18 h when it was then cooled and the solvents removed at reduced pressure. The residue was then dissolved in CHCl₃ and filtered through celite. Removal of the solvents under reduced pressure and column chromatography of the residue on silica gel (1:2 to 1:4 hexanes-ethyl acetate) yielded 1.84 g (82%) of a solid (m.p. 218°–219° C.) homogeneous by TLC and spectroscopic considerations. IR (KBr) 3240, 2982, 2889, 1700, 1640, 1596, 1567, 1522, 1480, 1470, 1456, 1440, 1388, 1367, 1361, 1335, 1318, 1258, 1209, 1158, 1137, 1119, 1088, 1079, 1039, 1012, 937, 837, 789, 704 cm⁻¹; ¹H NMR (400 MHz, CDCl₃)δ 7.42–7.26 (m, 9H), 7.01 (d, 2H, J=7.76 Hz), 6.45 (br s, 1H), 3.75 (m, 8H), 2.44 (s, 2H), 2.05–1.4 (m, 16H), 0.88 (s, 9H).

Elemental analysis for: C₃₉H₄₈N₂O₆. 0.5H₂O: Calc'd: C, 72.08; H, 7.60; N, 4.30; Found: C, 72.10; H, 7.56; N, 4.56.

METHOD K

Example 11

5-[[(2,4-Dimethoxyphenyl)amino][(R)-1[[[(1,1-dimethylethyl)dimethylsilyl]oxy]methyl]-2-phenylethyl]][4-(2-methylpropyl)phenyl]methyl]amino]methylene]-2,2-dimethyl-1,3-dioxane-4,6-dione Procedure 1

To a solution of 12.0 g (52.2 mmol) of L-phenylalanine ethyl ester hydrochloride in 350 mL of CH₂Cl₂ and 16.0 mL (0.115 mol) Et₃N at 0° C. was added 10.3 mL (52.2 mmol) of 4-isobutylbenzoyl chloride in 70 mL of CHCl₃. The reaction mixture stirred at 0° C. for 0.5 h then to room temperature for 20 h. The reaction mixture was then washed 3 times with H₂O, dried (MgSO₄) and the solvent removed at room temperature to yield 17.9 g (97%) of a solid which was used without further purification or characterization.

Procedure 2

To a solution of 9.9 g (28.0 mmol) of the amide produced in Method K, procedure 1 in 400 mL of toluene was added 20.6 mL (70.0 mmol) of a 3.4M solution of Red-Al, dropwise. After complete addition, the reaction mixture was refluxed for 19 h. The reaction mixture was cooled to room temperature and quenched with sat'd NH₄Cl. The toluene was removed at reduced pressure and the residue was poured into aqueous acid. The aqueous layer was then extracted 3 times with CHCl₃. The CHCl₃ layers were combined, dried (MgSO₄) and the solvent removed at reduced pressure. The salt obtained was washed with ether and added to aqueous NaOH. The aqueous layer was extracted 3 times with CH₂Cl₂ which were combined, dried (Na₂SO₄) and the solvent removed at reduced pressure. 5.4 g (65%) of a white solid was isolated and used accordingly.

Procedure 3

To a solution of 1.04 g (3.5 mmol) of the amine from Method K, procedure 2 in 20 mL of CH₂Cl₂ at 0° C. was added 2.1 g (7.35 mmol) of tert-butyldimethylsilyl chloride and 1.2 mL (8.4 mmol) of Et₃N. The reaction mixture was stirred at 0° C. for 5 min. then it was raised to room temperature and stirred for 18 h. The mixture was washed with H₂O, sat'd NaHCO₃ and sat'd NaCl, then dried (Na₂SO₄) and the solvent was removed at reduced pressure. The oily solid (1.3 g) was used without further purification or characterization.

Procedure 4

To a solution of 1.3 g (3.16 mmol) of the amine synthesized in Method K, procedure 3, in 50 mL of 1:1 acetonitrile-t-butanol was added 1.12 g (3.16 mmol) of 4-[(2,4-dimethoxyphenyl)amino]-5-methylthiomethylene-2,2-dimethyl-1,3-dioxane-4,6-dione, 0.55 g (1.89 mmol) HgSO₄ and 0.44 mL (3.16 mmol) of Et₃N. The reaction mixture stirred at reflux for 18 h. After cooling to room temperature, the reaction mixture was diluted with ethyl acetate and filtered through celite. The solvents were removed at reduced pressure and column chromatography of the residue on silica gel (1:2 to 2:1 ethyl acetate-hexane) yielded 1.0 g (44%) of a white solid (m.p. 123°–124° C.) homogeneous by spectroscopic considerations. IR (KBr) 3480, 2935, 2904, 2838, 1690, 1628, 1556, 1503, 1456, 1377, 1333, 1300, 1245, 1198, 1148, 1088, 1068, 1027, 920, 825, 773 cm⁻¹; ¹H NMR (400 MHz, CDCl₃) δ 7.33–7.23 (m, 8H), 7.11 (d, 2H, J=7.88 Hz), 6.44 (m, 2H), 4.84 (m, 1H), 4.64 (m, 1H), 4.18 (m, 1H), 3.77 (br s, 6H), 3.43 (m, 1H), 3.20 (m, 3H), 2.44 (d, 2H, J=7.28 Hz), 1.83 (m, 1H), 1.55 (br s, 6H), 0.88 (d, 6H, J=6.64 Hz), 0.75 (s, 9H), −0.12 (s, 3H), −0.15 (s, 3H).

Elemental analysis for: C₄₁H₅₆N₂O₇Si: Calc'd: C, 68.68; H, 7.87; N, 3.91; Found: C, 68.53; H, 7.86; N, 3.72.

METHOD L

Example 12

(R)-5-[[(2,4-Dimethoxyphenyl)amino][[(1R)-1-(hydroxymethyl)-2-phenylethyl][[4-(2-methyl-propyl)phenyl]methyl]amino]methylene]-2,2-dimethyl-1,3-dioxane-4,6-dione Procedure 1

To a solution of 0.57 g (0.8 mmol) of compound 11 in 20 mL of tetrahydrofuran at room temperature was added 0.96 mL (0.96 mol) of 1M tetrabutylammonium fluoride. After 66 h the reaction was halted and the solvents removed at reduced pressure. Column chromatography of the residue on silica gel (2% methanol-chloroform) yielded 0.43 g (90%) of a solid (m.p. 167°–168° C.); IR (KBr) 3250, 2941, 1683, 1625, 1565, 1505, 1448, 1429, 1412, 1376, 1351, 1302, 1258, 1201, 1152, 1093, 1029, 1019, 918, 824, 692 cm⁻¹.

Elemental analysis for: C₃₅H₄₂N₂O₇: Calc'd: C, 69.75; H, 7.02; N, 4.65; Found: C, 69.53; H, 7.21; N, 4.37.

METHOD M

Example 13

5-[[[3,5-Bis(1,1-dimethylethyl)-4-hydroxyphenyl]amino][(1-methyl(hexyl)][[4-(2-methylpropyl)-phenyl]amino]methylene]-2,2-dimethyl-1,3-dioxane-4,6-dione Procedure 1

To a solution of 1.8 g (7.25 mmol) of 5-[bis(methylthio)methylene]-2,2-dimethyl-1,3-dioxane-4,6-dione in 15 mL of degassed acetonitrile was added 2.0 g of 3,5-di-t-butyl-4-hydroxyaniline hydrochloride and 1.01 mL of Et$_3$N. The reaction mixture was allowed to stir at reflux for 48 h. The organic layer was then diluted with CHCl$_3$, washed twice with H$_2$O, dried (MgSO$_4$) and the solvents were removed at reduced pressure. Column chromatography (silica gel) was performed on the residue (3:1 to 2:1 hexanes-ethyl acetate) to yield 1.2 g of a yellow solid which by TLC showed two overlapping spots. This impure mixture was used without further purification or characterization.

Procedure 2

To a solution of 0.6 g (1.4 mmol) of the compound from Method M, procedure 1 in 20 mL of acetonitrile was added 0.37 g (1.4 mmol) of N-4-isobutylbenzyl-N—2-heptylamine, 0.22 g (0.77 mmol) HgSO$_4$ and 0.19 mL (1.4 mmol) of Et$_3$N. The reaction mixture was allowed to reflux for 19 h. Upon cooling the reaction mixture was diluted with EtOAc and filtered through celite and the solvents removed at reduced pressure. Column chromatography of the residue on silica gel (3:1 to 1:1 hexanes-ethyl acetate) yielded 0.36 g (46%) of a solid (dec. 202° C.) homogeneous by spectroscopic considerations. IR (KBr) 3600, 3402, 2944, 2908, 2858, 1693, 1618, 1566, 1459, 1428, 1382, 1361, 1249, 1225, 1196 1148, 1077, 1010, 920, 880 cm$^{-1}$; $^1$H NMR (400 MHz, CDCl$_3$) δ7.40–7.17 (m, 4H), 6.81 (br s, 2H), 5.20 (s, 2H), 4.56 (br m, 1H), 2.43 (d, 2H, J=7.04), 1.82–1.02 (m, 33H), 0.86 (m, 12H).

Elemental analysis for: C$_{39}$H$_{58}$N$_2$O$_5$: Calc'd: C, 73.78; H, 9.21; N, 4.41; Found: C, 73.43; H, 9.00; N, 4.31.

EXAMPLE 14

5-[[(2,4-Dimethoxyphenyl)amino][heptyl[(4-pentylphenyl)methyl]amino[methylene]-2,2-dimethyl-1,3-dioxane-4,6-dione This compound was synthesized according to the procedure outlined in Method D to yield a solid (m.p. 68°–71° C.).

Elemental analysis for: C$_{34}$H$_{48}$N$_2$O$_6$: Calc'd: C, 70.31; H, 8.33; N, 4.82; Found: C, 70.71; H, 8.46; N, 4.78.

Example 15

5-[[(2,4-Difluorophenyl)amino][[[4-(1,1-dimethylethyl)phenyl]methyl]heptylamino]methylene]-2,2-dimethyl-1,3-dioxane-4,6-dione This compound was synthesized according to the procedure outlined in Method C to yield a solid (m.p. 180°–181° C.).

Elemental analysis for: C$_{31}$H$_{40}$F$_2$N$_2$O$_4$: Calc'd: C, 68.61; H, 7.43; N, 5.16; Found: C, 68.80; H, 7.50; N, 5.05.

Example 16

5-[[[4-(Dimethylamino)-2,6-dimethylphenyl]amino][[[4-(1,1-dimethylethyl)phenyl]methyl]heptylamino]methylene]-2,2-dimethyl-1,3-dioxane-4,6-dione This compound was synthesized according to the procedure outlined in Method E to yield a solid (m.p. 185°–187° C.).

Elemental analysis for: C$_{35}$H$_{51}$N$_3$O$_4$: Calc'd: C, 72.75; H, 8.90; N, 7.27; Found: C, 73.00; H, 8.99; N, 7.15.

Example 17

5-[[[4-(Trifluoromethyl)phenyl]amino][heptyl[(4-pentylphenyl)methyl]amino]methylene]-2,2-dimethyl-1,3-dioxane-4,6-dione This compound was synthesized according to the procedure outlined in Method D to yield a solid (m.p. 88°–93° C.).

Elemental analysis for: C$_{33}$H$_{43}$F$_3$N$_2$O$_4$: Calc'd: C, 67.63; H, 7.56; N, 4.73; Found: C, 67.52; H, 7.69; N, 4.76.

Example 18

5-[[(2,4-Difluorophenyl)amino][[(4-hexylphenyl)methyl]heptylamino]methylene]-2,2-dimethyl-1,3-dioxane-4,6-dione This compound was synthesized according to the procedure outlined in Method G to yield a solid (m.p. 70°–72° C.).

Elemental analysis for: C$_{33}$H$_{44}$F$_2$N$_2$O$_4$: Calc'd: C, 69.45; H, 7.77; N, 4.91; Found: C, 69.37; H, 7.72; N, 4.90.

Example 19

5-[[(4-Butoxyphenyl)amino][[[4-(1,1-dimethylethyl)phenyl]methyl]heptylamino]methylene]-2,2-dimethyl-1,3-dioxane-4,6-dione This compound was synthesized according to the procedure outlined in Method G to yield a solid (m.p. 75°–78° C.).

Elemental analysis for: C$_{35}$H$_{50}$N$_2$O$_5$: Calc'd: C, 72.63; H, 8.71; N, 4.84; Found: C, 72.83; H, 8.88; N, 4.76.

Example 20

5-[[[[4-(1,1-Dimethylethyl)phenyl]methyl](1-methylhexyl)amino][3,4,5-trimethoxyphenyl)-amino]methylene]-2,2-dimethyl-1,3-dioxane-4,6-dione This compound was synthesized according to the procedure outlined in Method G to yield a solid (m.p. 176°–177° C.).

Elemental analysis for: C$_{34}$H$_{48}$N$_2$O$_7$: Calc'd: C, 68.43; H, 8.11; N, 4.69; Found: C, 68.71; H, 8.42; N, 4.86.

Example 21

5-[[[4-(Dimethylamino)phenyl]amino][[[4-(1,1-dimethylethyl)phenyl]methyl](1-methylhexyl)-amino]methylene]-2,2-dimethyl-1,3-dioxane-4,6-dione This compound was synthesized according to the procedure outlined in Method D to yield a solid (m.p. 119°–122° C.).

Elemental analysis for: C$_{33}$H$_{47}$N$_3$O$_4$: Calc'd: C, 72.10; H, 8.62; N, 7.64; Found: C, 72.28; H, 8.93; N, 7.64.

Example 22

5-[[[4-(Dimethylamino)phenyl]amino][heptyl[[[4-(3-methylbutyl)oxy]phenyl]methyl]amino]-methylene]-2,2-dimethyl-1,3-dioxane-4,6-dione This compound was synthesized according to the procedure outlined in Method F to yield a solid (m.p. 76°–80° C.).

Elemental analysis for: C$_{34}$H$_{49}$N$_3$O$_5$: Calc'd: C, 70.43; H, 8.51; N, 7.25; Found: C, 70.47; H, 8.71; N, 7.23.

Example 23

5-[[Heptyl[[4-[(3-methylbutyl)oxy]phenyl]methyl]amino][(3,4,5-trimethoxyphenyl)amino]methylene]-2,2-dimethyl-1,3-dioxane-4,6-dione This compound was synthesized according to the procedure outlined in Method F to yield a solid (m.p. 71°-74° C.).

Elemental analysis for: $C_{35}H_{50}N_2O_8$: Calc'd: C, 67.07; H, 8.04; N, 4.47; Found: C, 67.13; H, 7.97; N, 4.45.

Example 24

5-[[[[4-(1,1-Dimethylethyl)phenyl]methyl]heptylamino][[4-(pentyloxy)phenyl]amino]methylene]-2,2-dimethyl-1,3-dioxane-4,6-dione This compound was synthesized according to the procedure outlined in Method E to yield a solid (m.p. 78°-80° C.).

Elemental analysis for: $C_{36}H_{52}N_2O_5$: Calc'd: C, 72.94; H, 8.84; N, 4.72; Found: C, 72.86; H, 8.83; N, 4.68.

Example 25

5-[[[[4-(1,1-Dimethylethyl)phenyl]methyl]heptylamino][[4-(hexyloxy)phenyl]amino]methylene]-2,2-dimethyl-1,3-dioxane-4,6-dione This compound was synthesized according to the procedure outlined in Method E to yield a solid (m.p. 62°-65° C.).

Elemental analysis for: $C_{37}H_{54}N_2O_5$: Calc'd: C, 73.23; H, 8.97; N, 4.62; Found: C, 73.06; H, 8.84; N, 4.56.

Example 26

5-[[[[4-(1,1-Dimethylethyl)phenyl]methyl]heptylamino][[4-(phenylmethoxy)phenyl]amino]methylene]-2,2-dimethyl-1,3-dioxane-4,6-dione This compound was synthesized according to the procedure outlined in Method B to yield a solid (m.p. 81°-84° C.).

Elemental analysis for: $C_{38}H_{48}N_2O_5$: Calc'd: C, 74.48; H, 7.90; N, 4.57; Found: C, 74.49; H, 7.93; N, 4.51.

Example 27

5-[[(4-Butoxyphenyl)amino][[[4-(1,1-dimethylethyl)phenyl]methyl](1-methylhexyl)amino]-methylene]2,2-dimethyl-1,3-dioxane-4,6-dione This compound was synthesized according to the procedure outlined in Method D to yield a solid (m.p. 147°-151° C.).

Elemental analysis for: $C_{35}H_{50}N_2O_5$: Calc'd: C, 72.63; H, 8.71; N, 4.84; Found: C, 72.91; H, 8.76; N, 4.82.

Example 28

5-[[(4-Butoxyphenyl)amino][[[4-(1,1-dimethylethyl)phenyl]methyl](1.5-dimethylhexyl)amino]-methylene]-2,2-dimethyl-1,3-dioxane-4,6-dione This compound was synthesized according to the procedure outlined in Method D to yield a solid (m.p. 155°-156° C.).

Elemental analysis for: $C_{36}H_{52}N_2O_5$: Calc'd: C, 72.94; H, 8.84; N, 4.72; Found: C, 72.54; H, 8.83; N, 4.90.

Example 29

5-[[(2,4-Dimethoxyphenyl)amino][[[4-(1,1-dimethylethyl)phenyl]methyl](1,5-dimethylhexyl)-amino]methylene]-2,2-dimethyl-1,3-dioxane-4,6-dione This compound was synthesized according to the procedure outlined in Method D to yield a solid (m.p. 92°-95° C.).

Elemental analysis for: $C_{34}H_{48}N_2O_6$: Calc'd: C, 70.32; H, 8.33; N, 4.82; Found: C, 70.02; H, 8.28; N, 4.77.

Example 30

5-[[[[4-(1,1-Dimethylethyl)phenyl]methyl]heptylamino][[4-(trifluoromethyl)phenyl]amino]-methylene]-2,2-dimethyl-1,3-dioxane-4,6-dione This compound was synthesized according to the procedure outlined in Method B to yield a solid (m.p. 110°-112° C.).

Elemental analysis for: $C_{32}H_{41}F_3N_2O_4$: Calc'd: C, 66.88; H, 7.19; N, 4.87; Found: C, 66.59; H, 6.94; N, 4.72.

Example 31

5-[[(2,4-Dimethoxyphenyl)amino][heptyl[[4-(2-methylpropyl)phenyl]methyl]amino]methylene]-2,2-dimethyl-1,3-dioxane-4,6-dione This compound was synthesized according to the procedure outlined in Method G to yield a solid (m.p. 81°-84° C.).

Elemental analysis for: $C_{33}H_{46}N_2O_6$: Calc'd: C, 69.94; H, 8.18; N, 4.94; Found: C, 69.60; H, 8.25; N, 4.73.

Example 32

5-[[(2,4-Dimethoxyphenyl)amino][(1-methylhexyl)[[4-(2-methylpropyl)phenyl]methyl]amino]-methylene]-2,2-dimethyl-1,3-dioxane-4,6-dione This compound was synthesized according to the procedure outlined in Method G to yield a solid (m.p. 152°-155° C.).

Elemental analysis for: $C_{33}H_{46}N_2O_6$: Calc'd: C, 69.94; H, 8.18; N, 4.94; Found: C, 69.60; H, 8.30; N, 4.93.

Example 33

5-[[[2,6-Dimethyl-4-(dimethylamino)phenyl]amino][[[4-(2,2-dimethylpropyl)phenyl]methyl](1-methylhexyl)amino]methylene]-2,2-dimethyl-1,3-dioxane-4,6-dione This compound was synthesized according to the procedure outlined in Method G to yield a solid (m.p. 176°-177° C.).

Elemental analysis for: $C_{36}H_{53}N_3O_4$: Calc'd: C, 73.06; H, 9.03; N, 7.10; Found: C, 72.74; H, 9.05; N, 7.43.

Example 34

2,2-Dimethyl-5-[[(1-methylhexyl)[[4-(2-methylpropyl)phenyl]methyl]amino][[(3-phenylmethoxy)phenyl]amino]methylene]-4,6-dione This compound was synthesized according to the procedure outlined in Method G to yield a solid (m.p. 103°-105° C.).

Elemental analysis for: $C_{38}H_{48}N_2O_5$: Calc'd: C, 74.48; H, 7.89; N, 4.57; Found: C, 74.46; H, 7.86; N, 4.48.

Example 35

5-[[2,4-Dimethoxyphenyl]][[[4-(3-methylbutoxy)-phenyl]methyl](1-methylhexyl)amino]methylene]-2,2-dimethyl-1,3-dioxane-4,6-dione This compound was synthesized according to the procedure outlined in Method F to yield a solid (m.p. 133°-135° C.).

Elemental analysis for: $C_{34}H_{48}N_2O_4$: Calc'd: C, 68.43; H, 8.11; N, 4.69; Found: C, 68.48; H, 8.35; N, 4.66.

Example 36

5-[[[4-Dimethylamino)phenyl]amino][(1-hexylheptyl)[4-(2-methylpropyl)phenyl]methyl]-amino]methylene]-2,2-dimethyl-1,3-dioxane-4,6-dione This compound was synthesized according to the procedure outlined in Method G to yield a solid (m.p. 128°-130° C.).

Elemental analysis for: $C_{39}H_{59}N_3O_4$: Calc'd: C, 73.89; H, 9.38; N, 6.63; Found: C, 73.57; H, 9.38; N, 7.00.

Example 37

5-[[[(4-Dimethylamino)phenyl]amino][[[4-(2,2-dimethylpropyl)phenyl]methyl](1-methylhexyl)-amino]methylene]-2,2-dimethyl-1,3-dioxane-4,6-dione This compound was synthesized according to the procedure outlined in Method G to yield a solid (m.p. 145°-149° C.).

Elemental analysis for: $C_{34}H_{49}N_5O_4$: Calc'd: C, 72.43; H, 8.76; N, 7.45; Found: C, 72.12; H, 8.78; N, 7.38.

Example 38

5-[[[4-(Dimethylamino)phenyl]amino][[[4-(3-methylbutoxy)phenyl]methyl](1-methylhexyl)amino]methylene]-2,2-dimethyl-1,3-dioxane-4,6-dione This compound was synthesized according to the procedure outlined in Method F to yield a solid (m.p. 126°-128° C.).

Elemental analysis for: $C_{34}H_{49}N_3O_5$: Calc'd: C, 70.44; H, 8.52; N, 7.25; Found: C, 70.28; H, 8.55; N, 7.24.

Example 39

5-[[(2,4-Dimethoxyphenyl)amino][(1,5-dimethylhexyl)[4-(2-methylpropyl)phenyl]methyl]amino]methylene]-2,2-dimethyl-1,3-dioxane-4,6-dione This compound was synthesized according to the procedure outlined in Method G to yield a solid (m.p. 152°-154° C.).

Elemental analysis for: $C_{34}H_{48}N_2O_6$: Calc'd: C, 70.32; H, 8.33; N, 4.82; Found: C, 70.14; H, 8.30; N, 4.81.

Example 40

5-[[2,4-Dimethoxyphenyl)amino][(1-methylhexyl)[(4'-pentylphenyl)methyl]amino]methylene]-2,2-dimethyl-1,3-dioxane-4,6-dione This compound was synthesized according to the procedure outlined in Method G to yield a solid (m.p. 130°-132° C.).

Elemental analysis for: $C_{34}H_{48}N_2O_6$: Calc'd: C, 70.32; H, 8.33; N, 4.82; Found: C, 70.10; H, 8.52; N, 4.89.

Example 41

5-[[[4-(Dimethylamino)phenyl]amino][(1-methylhexyl)[(4-pentylphenyl)methyl]amino]-methylene]-2,2-dimethyl-1,3-dioxane-4,6-dione This compound was synthesized according to the procedure outlined in Method G to yield a solid (m.p. 163°-164° C.).

Elemental analysis for: $C_{34}H_{49}N_3O_4$: Calc'd: C, 72.43; H, 8.76; N, 7.45; Found: C, 72.73; H, 9.11; N, 7.43.

Example 42

5-[[[4-(Dimethylamino)phenyl]amino][[[4-(2-methylpropyl)phenyl]methyl](1,5-dimethylhexyl)-amino]methylene]-2,2-dimethyl-1,3-dioxane-4,6-dione This compound was synthesized according to the procedure outlined in Method G to yield a solid (m.p. 175°-177° C.).

Elemental analysis for: $C_{34}H_{49}N_3O_4$: Calc'd: C, 72.44; H, 8.76; N, 7.45; Found: C, 72.60; H, 9.07; N, 7.56.

Example 43

5-[[[4-(Hexyloxy)phenyl]amino][(1-methylhexyl)[[4-(2-methylpropyl)phenyl]methyl]amino]-methylene]-2,2-dimethyl-1,3-dioxane-4,6-dione This compound was synthesized according to the procedure outlined in Method G to yield a solid (m.p. 63°-66° C.).

Elemental analysis for: $C_{37}H_{54}N_2O_5$: Calc'd: C, 73.23; H, 8.97; N, 4.62; Found: C, 73.39; H, 9.28; N, 4.76.

Example 44

5-[[[(4-Butylphenyl)methyl](5-hydroxy-1,5-dimethylhexyl)amino][(2,4-dimethoxyphenyl)-amino]methylene]-2,2-dimethyl-1,3-dioxane-4,6-dione This compound was synthesized according to the procedure outlined in Method G. to yield a solid, hemihydrate (m.p. 85°-88° C.).

Elemental analysis for: $C_{34}H_{48}N_2O_7 \cdot 0.5H_2O$: Calc'd: C, 67.41; H, 8.15; N, 4.62; Found: C, 67.21; H, 7.79; N, 4.64.

Example 45

5-[[[(4-Butylphenyl)methyl](5-hydroxy-1,5-dimethylhexyl)amino][[4-(dimethylamino)phenyl]-amino]methylene]-2,2-dimethyl-1,3-dioxane-4,6-dione This compound was synthesized according to the procedure outlined in Method G to yield a solid, hydrate (m.p. 92°-95° C.).

Elemental analysis for: $C_{34}H_{49}N_3O_5 \cdot H_2O$: Calc'd: C, 68.31; H, 8.60; N, 7.03; Found: C, 68.26; H, 8.61; N, 7.31.

Example 46

5-[[[4-(Dimethylamino)-2-methylphenyl]amino][(1-methylhexyl)[4-(2-methylpropyl)phenyl]-methyl]amino]methylene]-2,2-dimethyl-1,3-dioxane-4,6-dione This compound was synthesized according to the procedure outlined in Method E to yield a solid (m.p. 122°-124° C.).

Elemental analysis for: $C_{34}H_{49}N_3O_4$: Calc'd: C, 72.43; H, 8.76; N, 7.45; Found: C, 72.24; H, 8.96; N, 7.54.

Example 47

5-[[[4-(Dimethylamino)-2-methylphenyl]amino][[[4-(2,2-dimethylpropyl)phenyl]methyl]-(1-methylhexyl)amino]methylene]-2,2-dimethyl-1,3-dioxane-4,6-dione This compound was synthesized according to the procedure outlined in Method E to yield a solid (m.p. 125°–128° C.).

Elemental analysis for: $C_{35}H_{51}N_3O_4$: Calc'd: C, 72.75; H, 8.89; N, 7.27; Found C, 72.41; H, 9.22; N, 7.32.

Example 48

5-[[(2,4-Dimethoxyphenyl)amino][[[4-(2,2-dimethylpropyl)phenyl]methyl]heptylamino]-methylene]-2,2-dimethyl-1,3-dioxane-4,6-dione This compound was synthesized according to the procedure outlined in Method B to yield a solid (m.p. 86°–89° C.).

Elemental analysis for: $C_{39}H_{48}N_2O_6$: Calc'd: C, 70.32; H, 8.33; N, 4.82; Found: C, 70.18; H, 8.50; N, 4.91.

Example 49

5-[[[4-((Dimethylamino)phenyl]amino][[[4-(2-methylpropyl)phenyl]methyl][1-(phenylmethyl)-4-piperidinyl]amino]methylene]-2,2-dimethyl-1,3-dioxane-4,6-dione This compound was synthesized according to the procedure outlined in Method H to yield a solid (m.p. 140°–142° C.).

Elemental analysis for: $C_{38}H_{48}N_4O_4$: Calc'd: C, 73.05; H, 7.74; N, 8.97; Found: C, 72.87; H, 7.83; N, 8.96.

Example 50

5-[[(2,4-Dimethoxyphenyl)amino][[1-methyl-2-(4-morpholinyl)ethyl][[4-(2-methylpropyl)-phenyl]methyl]amino]methylene]-2,2-dimethyl-1,3-dioxane-4,6-dione This compound was synthesized according to the procedure outlined in Method H to yield a solid (m.p. 108°–112° C.).

Elemental analysis for: $C_{33}H_{45}N_3O_7$: Calc'd: C, 66.53; H, 7.61; N, 7.05; Found: C, 66.71; H, 7.68; N, 6.95.

Example 51

5-[[[4-Dimethylamino)phenyl]amino][[1-methyl-2-(4-morpholinyl)ethyl][[4-(2-methylpropyl)-phenyl]methyl]amino]methylene]-2,2-dimethyl-1,3-dioxane-4,6-dione This compound was synthesized according to the procedure outlined in Method H to yield a solid (m.p. 144°–148° C.).

Elemental analysis for: $C_{33}H_{46}N_4O_5$: Calc'd: C, 68.49; H, 8.01; N, 9.68; Found: C, 68.27; H, 8.02; N, 9.52.

Example 52

5-[[(2,4-Dimethoxyphenyl)amino][(5-hydroxy-1,5-dimethylhexyl)][[4-(2-methylpropyl)phenyl]-methyl]amino]methylene]-2,2-dimethyl-1,3-dioxane-2,4-dione This compound was synthesized according to the procedure outlined in Method G to yield a solid, hydrate (m.p. 80°–83° C.).

Elemental analysis for: $C_{34}H_{48}N_2O_7 \cdot H_2O$: Calc'd: C, 66.42; H, 8.20; N, 4.56; Found: C, 66.38; H, 7.87; N, 4.44.

Example 53

5-[[[4-(Dimethylamino)phenyl]amino][(5-hydroxy-1,5-dimethylhexyl)][[4-(2-methylpropyl)-phenyl]methyl]amino]methylene]-2,2-dimethyl-1,3-dioxane-4,6-dione This compound was synthesized according to the procedure outlined in Method G to yield a solid, 0.75 hydrate (m.p. 110°–111° C.).

Elemental analysis for: $C_{34}H_{49}N_3O_5 \cdot 0.75H_2O$: Calc'd: C, 68.83; H, 8.58; N, 7.08; Found: C, 68.84; H, 8.20; N, 7.02.

Example 54

5-[[[4-(Dimethylamino)-2-methylphenyl]amino][(1-methylhexyl)][(4-pentylphenyl)methyl]-amino]methylene]-2,2-dimethyl-1,3-dioxane-4,6-dione This compound was synthesized according to the procedure outlined in Method G to yield a solid (m.p. 115°–117° C.).

Elemental analysis for: $C_{35}H_{51}N_3O_4$; Calc'd: C, 72.76; H, 8.90; N, 7.27; Found: C, 72.65; H, 9.02; N, 7.17.

Example 55

5-[[(2,4-Dimethoxyphenyl)amino][heptyl[[4-(3-methylbutyl)phenyl]methyl]amino]methylene]-2,2-dimethyl-1,3-dioxane-4,6-dione This compound was synthesized according to the procedure outlined in Method G to yield a solid (m.p. 129°–131° C.).

Elemental analysis for: $C_{34}H_{48}N_2O_6$; Calc'd: C, 70.32; H, 8.33; N, 4.82; Found: C, 70.55; H, 8.49; N, 5.00.

Example 56

5-[[(2,4-Dimethoxyphenyl)amino][[[4-(3-methylbutyl)-phenyl]methyl](1-methylhexyl)amino]-methylene]-2,2-dimethyl-1,3-dioxane-4,6-dione This compound was synthesized according to the procedure outlined in Scheme G to yield a solid (m.p. 124–126).

Elemental analysis for: $C_{34}H_{48}N_2O_6$; Calc'd: C, 70.32; H, 8.33; N, 4.82; Found: C, 70.32; H, 8.48; N, 4.85.

Example 57

5-[[[4-(Dimethylamino)phenyl]amino][[[4-(3-methylbutyl)phenyl]methyl](1-methylhexyl)-amino]methylene]-2,2-dimethyl-1,3-dioxane-4,6-dione This compound was synthesized according to the procedure outlined in Method G to yield a solid (m.p. 173°–175° C.).

Elemental analysis for: $C_{34}H_{49}N_3O_4$: Calc'd: C, 72.43; H, 8.76; N, 7.45; Found: C, 72.47; H, 8.81; N, 7.48.

Example 58

5-[[(2,4-Dimethoxyphenyl)amino][(1-methylhexyl)][[4-(2-methylpropoxy)phenyl]methyl]-amino]methylene]-2,2-dimethyl-1,3-dioxane-4,6-dione This compound was synthesized according to the procedure outlined in Method G to yield a solid (m.p. 147°–149° C.).

Elemental analysis for: $C_{33}H_{46}N_2O_7$: Calc'd: C, 68.02; H, 7.96; N, 4.81; Found: C, 68.13; H, 8.03; N, 4.85.

Example 59

5-[[[[4-(1,1-Dimethylethyl)phenyl]methyl]heptylamino][(2,4,6-trimethoxyphenyl)amino]-methylene]-2,2-dimethyl-1,3-dioxane-4,6-dione This compound was synthesized according to the procedure outlined in Method B to yield a solid (m.p. 145°–146° C.).

Elemental analysis for: $C_{34}H_{48}N_2O_7$: Calc'd: C, 68.43; H, 8.11; N, 4.69; Found: C, 68.24; H, 8.02; N, 4.57.

Example 60

5-[[(2,4-Dimethoxyphenyl)amino][[[4-(2,2-dimethylpropyl)phenyl]methyl](1-ethylpentyl)amino]-methylene]-2,2-dimethyl-1,3-dioxane-4,6-dione This compound was synthesized according to the procedure outlined in Method G to yield a solid (m.p. 151°–153° C.).

Elemental analysis for: $C_{34}H_{48}N_2O_6$: Calc'd: C, 70.32; H, 8.33; N, 4.82; Found: C, 70.25; H, 8.11; N, 4.82.

Example 61

5-[[[[4-(Dimethylamino)-2-methylphenyl]amino][[[4-(3-methylbutyl)phenyl]methyl](1-methylhexyl)amino]methylene]-2,2-dimethyl-1,3-dioxane-4,6-dione This compound was synthesized according to the procedure outlined in Method G to yield a solid (m.p. 118°–119° C.).

Elemental analysis for: $C_{35}H_{51}N_3O_4$: Calc'd: C, 72.76; H, 8.90; N, 7.27; Found: C, 72.63; H, 9.01; N, 7.33.

Example 62

5-[[[[4-(Dimethylamino)phenyl]amino][[[4-(2,2-dimethylpropyl)phenyl]methyl](1-ethylpentyl)-amino]methylene]-2,2-dimethyl-1,3-dioxane-4,6-dione This compound was synthesized according to the procedure outlined in Method G to yield a solid (m.p. 120°–124° C.).

Elemental analysis for: $C_{34}H_{49}N_3O_4$: Calc'd: C, 72.43; H, 8.76; N, 7.45; Found: C, 72.31; H, 8.54; N, 7.44.

Example 63

5-[[[[4-Dimethylamino)phenyl]amino][(1-methylhexyl)[[4-(2-methylpropoxy)phenyl]methyl]amino]methylene]-2,2-dimethyl-1,3-dioxane-4,6-dione This compound was synthesized according to the procedure outlined in Method F to yield a solid (m.p. 139°–141° C.).

Elemental analysis for: $C_{33}H_{47}N_3O_5$: Calc'd: C, 70.06; H, 8.37; N, 7.43; Found: C, 70.11; H, 8.37; N, 7.42.

Example 64

5-[[(2,4-Dimethylphenyl)amino][[[4-(2,2-dimethylpropyl)phenyl]methyl](1-methylhexyl)amino]-methylene]-2,2-dimethyl-1,3-dioxane-4,6-dione This compound was synthesized according to the procedure outlined in Method G to yield a solid (m.p. 147°–148° C.).

Elemental analysis for: $C_{39}H_{48}N_2O_4$: Calc'd: C, 74.42; H, 8.82; N, 5.10; Found: C, 74.45; H, 8.89; N, 5.18.

Example 65

5-[[Decyl[[4-(1,1-diethylethyl)phenyl]methyl]amino][(2,4-dimethoxyphenyl)amino]methylene]-2,2-dimethyl-1,3-dioxane-4,6-dione This compound was synthesized according to the procedure outlined in Method B to yield a solid (m.p. 81°–84° C.).

Elemental analysis for: $C_{36}H_{52}N_2O_6$: Calc'd: C, 71.02; H, 8.61; N, 4.60; Found: C, 71.09; H, 8.51; N, 4.59.

Example 66

5-[[[4-(Dimethylamino)-2-methylphenyl]amino][[[4-(2,2-dimethylpropyl)phenyl]methyl](1-ethylpentyl)amino]methylene]-2,2-dimethyl-1,3-dioxane-4,6-dione This compound was synthesized according to the procedure outlined in Method G to yield a solid (m.p. 133°–136° C.).

Elemental analysis for: $C_{35}H_{51}N_3O_4$: Calc'd: C, 72.76; H, 8.90; N, 7.27; Found: C, 72.38; H, 8.69; N, 6.98.

Example 67

5-[[[[4-(1,1-Dimethylethyl)phenyl]methyl]hexylamino][(4-Fluorophenyl)amino]methylene]-2,2-dimethyl-1,3-dioxane-4,6-dione This compound was synthesized according to the procedure outlined in Method B to yield a solid (mp 196°–198° C.).

Elemental analysis for: $C_{31}H_{41}FN_2O_4$: Calc'd: C, 70.97; H, 7.88; N, 5.34; Found: C, 70.82; H, 7.70; N, 5.32.

Example 68

5-[[(2,4-Dimethylphenyl)amino][(1-methylhexyl)[[4-2-methylpropoxy)phenyl]methyl]amino]-methylene]-2,2-dimethyl-1,3-dioxane-4,6-dione This compound was synthesized according to the procedure outlined in Method F to yield a solid (mp 109°–112° C.).

Elemental analysis for: $C_{33}H_{46}N_2O_5$: Calc'd: C, 71.97; H, 8.42; N, 5.09; Found: C, 71.80; H, 8.40; N, 5.08.

Example 69

5-[[[[4-(1,1-Dimethylethyl)phenyl]methyl]heptylamino][3,4,5-trimethoxyphenyl)amino]-methylene]-2,2-dimethyl-1,3-dioxane-4,6-dione This compound was synthesized according to the procedure outlined in Method B to yield a solid (mp 162°–163° C.).

Elemental analysis for: $C_{34}H_{48}FN_2O_7$: Calc'd: C, 68.43; H, 8.11; N, 4.69; Found: C, 68.32; H, 8.14; N, 4.55.

Example 70

5-[[(2,4-Dimethoxyphenyl)amino][[[4-(1,1-dimethylethyl)phenyl]methyl]((Z)-9-octadecenyl)-amino]methylene]-2,2-dimethyl-1,3-dioxane-2,4-dione This compound was synthesized according to the procedure outlined in Method B to yield a solid (mp 58°–61° C.).

Elemental analysis for: $C_{44}H_{66}FN_2O_6$: Calc'd: C, 73.50; H, 9.25; N, 3.90; Found: C, 73.62; H, 9.34; N, 3.89.

Example 71

5-[[(2,4-Dimethoxyphenyl)amino][[(R)-1-[[[(1,1-dimethylethyl)dimethylsilyl]oxy]methyl]-3-methylbutyl]][[4-(2-methylpropyl)phenyl]methyl]amino]methylene-2,2-dimethyl-1,3-dioxane-4,6-dione This compound was synthesized according to the procedure outlined in Method K to yield a solid (mp 114°-115° C.).

Elemental analysis for: $C_{38}H_{58}N_2O_7Si$: Calc'd: C, 66.83; H, 8.56; N, 4.10; Found: C, 66.80; H, 8.64; N, 4.01.

Example 72

5-[[(2,4-Dimethoxyphenyl)amino][[[4-(3-methylbutyl)phenyl]methyl][3-methyl-1-(2-methylpropyl)butyl]amino]methylene]-2,2-dimethyl-1,3-dioxane-4,6-dione This compound was synthesized according to the procedure outlined in Method G to yield a solid (mp 116°-118° C.).

Elemental analysis for: $C_{36}H_{52}N_2O_6$: Calc'd: C, 71.02; H, 8.61; N, 4.60; Found: C, 70.68; H, 8.66; N, 4.63.

Example 73

5-[[[4-Dimethylamino)phenyl]amino][[[4-(3-methylbutyl)phenyl]methyl][3-methyl-1-(2-methylpropyl)butyl]amino]methylene]-2,2-dimethyl-1,3-dioxane-4,6-dione This compound was synthesized according to the procedure outline in Method G to yield a solid (mp 116°-118° C.).

Elemental analysis for: $C_{36}H_{53}N_3O_4$: Calc'd: C, 73.06; H, 9.03; N, 7.10; Found: C, 73.18; H, 9.31; N, 7.40.

Example 74

(R)-5-[[(2,4-Dimethoxyphenyl)amino][[1-(hydroxymethyl)-3-methylbutyl]][[4-(2-methylpropyl)-phenyl]methyl]amino]methylene]-2,2-dimethyl-1,3-dioxane-4,6-dione This compound was synthesized according to the procedure outlined in Method G to yield a solid (mp 116°-118° C.).

Elemental analysis for: $C_{32}H_{44}N_2O_7$; Calc'd: C67.58; H, 7.80; N, 4.93; Found: C, 67.43; H, 8.02; N, 4.80.

Example 75

5-[[[3,5-Bis(1,1-dimethylethyl)-4-hydroxyphenyl]amino][(1-methylhexyl)[[4-(2,2-dimethyl-propyl)phenyl]methyl]amino]methylene]-2,2-dimethyl-1,3-dioxane-4,6-dione This compound was synthesized according to the procedure outlined in Method M to yield a solid (mp 204°-206° C.).

Elemental analysis for: $C_{40}H_{60}N_2O_5$; Calc'd: C, 74.04; H, 9.32; N, 4.32; Found: C, 73.96; H, 9.45; N, 4.57.

Example 76

5-[[[3,5-Bis(1,1-dimethylethyl)-4-hydroxyphenyl]amino][[[4-(2,2-dimethylpropyl)phenyl]methyl]heptylamino]methylene]-2,2-dimethyl-1,3-dioxane-4,6-dione Procedure 1

To a solution of 6.4 g (25.8 mmol) of 5-[bis(methylthio)methylene]-2,2-dimethyl-1,3-dioxane-4,6-dione and 4.84 (56.0 mmol) of sodium bicarbonate in 10 mL of degassed DMSO was added 10.0 g (36.0 mmol) of 3,5-di-t-butyl-4-hydroxyaniline hydrochloride in 30 mL degassed DMSO over a 5 h period at room temperature. Stirring was continued for an additional 19 h. The reaction mixture was poured into cold $H_2O$ and the product filtered. The solid was dried and dissolved in ethyl acetate and filtered again. The solvent was removed at reduced pressure and the residue submitted to a column chromatography on silica gel (3:1 to 2:1 Hexane-ethyl acetate) to yield 9.8 g (90%) of a solid that was used without further purification.

Procedure 2

To a solution of 0.84 g (2.0 mmol) of the compound from above in 20 mL of 1:1 t-butanol-acetonitrile was added 0.55 g (2.0 mmol) of N-4-neopentylbenzyl-N-heptylamine, 0.36 g (1.2 mmol) of mercuric sulfate and 0.28 mL (2.0 mmol) of triethylamine. The reaction mixture was allowed to reflux for 4 hours. The solution was cooled to room temperature, diluted with ethyl acetate and filtered through celite. The solvent was removed under reduced pressure and column chromatography of the residue on silica gel (1:2 to 2:1 ethyl acetate-hexanes) yielded 0.98 g (75%) of a pale yellow solid (m.p. 96°-100° C.) homogenous by spectroscopic considerations. IR (KBr): 3220, 2950, 2860, 1696, 1624, 1465, 1429, 1382, 1358, 1262, 1229, 1198, 1112, 1086, 921 and 779 cm$^{-1}$; $^1$H NMR (400 MHz, CDCl$_3$): d 7.18 (d, 2H, J=7.88 Hz), 7.09 (d, 2H, J=8.08 Hz), 6.89 (s, 2H), 5.22 (s, 1H), 4.39 (s, 2H), 3.14 (m, 2H), 2.46 (s, 2H), 1.70-1.55 (m, 8H), 1.38 (s, 18H), 1.24-1.14 (m, 8H) (s, 9H) (t, 3H, J=6.84 Hz).

Elemental analysis for: $C_{40}H_{60}N_2O_5$; Calc'd: C, 74.04; H, 9.32; N, 4.32; Found: C, 73.93; H, 9.39; N, 4.26.

| In Vitro | IC$_{50}$ (μM) |
| --- | --- |
| 96% (25 μM) | 0.06 |

Example 77

5-[[[3,5-Bis(1,1-dimethylethyl)-4-hydroxyphenyl]amino]hexyl[[4-(2-methylpropyl)phenyl]methyl]amino]methylene]-2,2-dimethyl-1,3-dioxane-4,6-dione This compound was synthesized according to the procedure outlined in Example 76 above to yield a solid (mp 120°-122° C.).

Elemental analysis for: $C_{38}H_{56}N_2O_5$: Calc'd: C, 73.51; H, 9.09; N, 4.51; Found: C, 73.37; H, 8.80; N, 4.57.

Example 78

5-[[Heptyl[[4-(3-methylbutoxy)phenyl]methyl]amino][[3-(phenylmethoxy)phenyl]amino]methylene]-2,2-dimethyl-1,3-dioxane-4,6-dione This compound was synthesized according to the procedure outlined in Method F to yield a solid (mp 58°-60° C.).

Elemental analysis for: $C_{39}H_{50}N_2O_6$; Calc'd: C, 72.87; H, 7.84; N, 4.36; Found C, 72.24; H, 7.82; N, 4.33.

Example 79

5-[[[3,5-Bis(1,1-dimethylethyl)-4-hydroxyphenyl]amino][[[4-(2,2-dimethylpropyl)phenyl]methyl]hexylamino]methylene]-2,2-dimethyl-1,3-dioxane-4,6-dione This compound was synthesized according to the procedure outlined in Example 76 to yield a solid (mp 162°-164° C.).

Elemental analysis for: $C_{39}H_{58}N_2O_5$; Calc'd: C, 73.78; H, 9.21; N, 4.41; Found: C, 73.47; H, 8.98; N, 4.16.

Example 80

5-[[[3,5-Bis(1,1-dimethylethyl)-4-hydroxyphenyl]amino][cyclohexyl[[4-(2,2-dimethylpropyl)-phenyl]methyl]amino]methylene]-2,2-dimethyl-1,3-dioxane-4,6-dione To a solution of 7.06 g (71.2 mmol) of cyclohexylamine and 14.41 g (142.4 mmol) of triethylamine in 150 mL of $CHCl_3$ at 0° C. was added 14.0 g (71.2 mmol) of 4-neopentylbenzoyl chloride dropwise. The reaction mixture stirred at 0° C. for 1 hour then to room temperature for 67 hours. This mixture was added to 150 mL of $H_2O$ and the organic layer was separated then washed with 150 mL of $H_2O$. The chloroform layer was dried ($Na_2SO_4$) and the solvents were removed at reduced pressure. The solid obtained was used without further purification or characterization.

To a solution of 19.9 g (71.2 mmol) of the amide from the preceding paragraph, 250 mL of toluene at 0° C. was added 41.9 mL of 3.4M Red-Al dropwise. After addition the solution stirred at 0° C. for 10 minutes and was warmed to reflux for 18 hours. The reaction mixture was quenched with aqueous $NH_4Cl$ and the solvent removed at reduced pressure. The residue was taken up in 350 mL of $H_2O$ and acidified to pH=2 with concentrated HCl. The aqueous layer was extracted with $CHCl_3$ (3×150 mL) which were combined, dried ($MgSO_4$) and the solvent removed at reduced pressure. The amine-hydrochloride salt was triturated with hexane then filtered. The salt was added to 600 mL of $H_2O$ and the pH raised to 14 with solid NaOH. This was extracted with diethyl ether (4×125 mL). The combined ether layers were dried ($Na_2SO_4$) and the solvent removed at reduced pressure. The amine was used without further purification or characterization.

To a solution of 0.8 g (1.0 mmol) of the compound from Method M, procedure 1 in 20 mL of acetonitrile was added 0.49 g (1.9 mmol) of N-4-neopentylbenzyl-N-cyclohexylamine, 0.34 g (1.14 mmol) of mercuric sulfate and 0.26 mL (1.9 mmol) triethylamine. This solution was stirred at reflux for 2.5 hours. The solution was cooled to room temperature and filtered through celite which was washed with ethyl acetate. The solvents were removed at reduced pressure and column chromatography of the residue on silica gel (40% hexanes-3% triethylamine-57% ethyl acetate), yielded 1.0 g (83%) which was recrystallized from diethyl ether (mp 165°–167° C.). IR (KBr) 3430, 2945, 2858, 1625, 1568, 1482, 1431, 1382, 1253, 1229, 1196, 1157, 1091, 1006, 926, 886, 780 $cm^{-1}$. $^1H$ NMR (400 MHz, $CDCl_3$): δ 7.26–7.13 (m, 4H), 6.87 (s, 2H), 5.22 (s, 1H), 4.64 (br s, 2H), 4.14 (br s, 1H), 2.47 (s, 2H), 2.08 (m, 2H), 1.76 (m, 2H), 1.57 (s, 6H), 1.42–1.25 (m, 27H), 0.88 (s, 9H).

Elemental Analysis for: $C_{39}H_{56}N_2O_5$: Calc'd: C, 74.01; H, 8.92; N, 4.43; Found: C, 74.19; H, 8.66; N, 4.42.

METHOD N

Example 81

5-[(3,5-Di-tert-butyl-4-hydroxy-phenylamino)-(quinolin-3-ylamino)-methylene]-2,2-dimethyl-[1,3]dioxane-4,6-dione Procedure 1

To a solution of 6.4 g (25.8 mmol) of 5-[bis(methylthio)methylene]-2,2-dimethyl-1,3-dioxane-4,6-dione and 4.84 g (56.0 mmol) of sodium bicarbonate in 10 mL of degassed DMSO was added 10.0 g (36.0 mmol) of 3,5-di-t-butyl-4-hydroxyaniline hydrochloride in 30 mL of degassed DMSO over a 5 hour period at room temperature. Stirring was continued for an additional 19 hours. The reaction mixture was poured into cold $H_2O$ and the product filtered. The solid was dried and dissolved in ethyl acetate and filtered again. The solvent was removed at reduced pressure and the residue submitted to column chromatography on silica gel (3:1 to 2:1 hexane-ethyl acetate) to yield 9.8 g (90%) of a solid that was used without further purification.

Procedure 2

To a solution of 0.41 g (0.97 mmol) of the product from Method A, procedure 1, was added 0.14 g (0.97 mmol) of 3-aminoquinoline, 0.16 g (0.97 mmol) of triethylamine, 0.16 g (0.53 mmol) of $HgSO_4$ and 20 mL of acetonitrile. The reaction mixture was allowed to reflux for 16 hours. The reaction mixture was cooled to room temperature and diluted with ethyl acetate and filtered through Celite ®. The solvents were removed at reduced pressure and the residue was chromatographed on silica gel (50:50 ethylacetate-hexanes) to yield 0.37 g (74%) of a solid which was recrystallized with ethyl acetate-hexanes (m.p. 203° C.) IR (KBr) 3460, 2945, 1647, 1606, 1421, 1389, 1337, 1313, 1251, 1202, 1178, 933, 890, 801, and 758 $cm^{-1}$. $^1H$ NMR (400 $MH_2$, $CDCl_3$) δ 12.01 (brs, 1H), 11.76 (brs, 1H), 8.50 (d, 1H, J=2.28 Hz), 7.88 (d, 1H, J=8.5 Hz), 7.56 (t, 1H, J=6.57 Hz), 7.45 (m, 3H), 6.65 (s, 2H), 4.76 (s, 1H), 1.79 (s, 6H), 1.09 (s, 18H).

Elemental analysis for $C_{30}H_{35}N_3O_5$: Calc'd: C, 69.61;H, 6.82; N, 8.12; Found: C, 69.56; H, 6.81; N, 8.02.

Substitution of 5-aminoquinoline, 6-aminoquinoline or 8-aminoquinoline for the 3-aminoquinoline of the preceding paragraph affords 5-[(3,5-di-tert-butyl-4-hydroxy-phenylamino)-(quinolin-5-ylamino)-methylene]-2,2-dimethyl-[1,3]dioxane-4,6-dione, 5-[(3,5-di-tert-butyl-4-hydroxy-phenylamino)-(quinolin-6-ylamino)-methylene]-2,2-dimethyl-[1,3]dioxane-4,6-dione and 5-[(3,5-di-tert-butyl-4-hydroxy-phenylamino)-(quinolin-8-ylamino)-methylene]-2,2-dimethyl-[1,3]dioxane-4,6-dione, respectively.

Example 82

5-[(3,5-Di-tert-butyl-4-hydroxy-phenylamino)-(pyridin-3-ylamino)-methylene]2,2-dimethyl-[1,3]dioxane-4,6-dione Procedure 1

To a solution of 1.53 g (3.64 mmol) of the product from Method A, Procedure 1, was added 0.34 g (3.64 mmol) of 3-aminopyridine, 0.37 g (3.64 mmol) of triethylamine, 0.59 g (2.0 mmol) of $HgSO_4$ and 20 mL of acetonitrile. The reaction mixture waS allowed to reflux for 16 hours and then cooled to room temperature. The mixture was diluted with ethyl acetate and filtered through Celite ®. The solvents were removed at reduced pressure and the residue chromatographed on silica gel (1:1 ethyl acetate-hexanes) to yield after recrystallization from ethyl acetate-hexanes, 1.20 g (70%) of a white solid (m.p. 164° C.). IR (KBr) 3420, 2950, 1688, 1637, 1579, 1522, 1432, 1391, 1318, 1265, 1200, 1082, 931, 802 and 708 $cm^{-1}$. $^1H$ NMR (400 MHz), $CDCl_3$ δ 11.84 (brs, 1H), 11.74 (brs, 1H), 8.21 (d, 1H, J=2.80 Hz), 8.12 (dd, 1H, J=1.2, 4.67 $H_2$), 7.05 (dt, 1H, J=1.86 8.09 Hz), 6.83 (dd, 1H, J=4.77, 8.09 Hz), 6.65 (s, 2H), 5.05 (s, 1H), 1.77 (s, 6H), 1.26 (s, 18H).

Elemental analysis for $C_{26}H_{35}N_3O_5$: Calc'd: C, 66.78; H, 7.11; N, 8.99; Found: C, 66.39; H, 7.00; N, 8.84.

Following this procedure with the exception that 2-aminopyridine or 4-aminopyridine is used instead of 3-aminopyridine affords 5-[(3,5-di-tert-butyl-4-hydroxy-phenylamino)-(pyridin-2-ylamino)-methylene]-2,2-dimethyl-[1,3]dioxane-4,6-dione and 5-[(3,5-di-tert-butyl-4-hydroxy-phenylamino)-(pyridin-4-ylamino)-methylene-2,2-dimethyl-[1,3]dioxane-4,6-dione, respectively.

Example 83

5-[(3,5-Di-tert-butyl-4-hydroxy-phenylamino)-(methyl-pyridin-2-ylamino)-methylene]-2,2-dimethyl-[1,3]dioxane-4,6-dione Procedure 1

To a solution of 0.77 g (1.83 mmol) of the product from Method A, Procedure 1, in 20 mL of acetonitrile was added 0.20 g (1.83 mmol) of 2-(methylamino)pyridine, 0.18 g (1.83 mmol) of triethylamine and 0.3 g (1.0 mmol) of $HgSO_4$. The reaction mixture was allowed to stir at reflux for 16 hours. The mixture was cooled to room temperature and diluted with ethyl acetate. This was filtered through Celite® and the solvents were removed at reduced pressure. Chromatography of the residue on silica gel (1:1 ethyl acetate-hexanes) gave after recrystallization (ethyl acetate-hexanes) 0.41 g (47%) of a yellow-green solid (m.p. 189°-195° C.). IR (KBr) 3395, 2999, 2958, 2918, 1719, 1653, 1591, 1558, 1472, 1453, 1432, 1385, 1378, 1278, 1197, 1152, 1133, 1099, 1052, 1035, 931 and 779 $cm^{-1}$. $^1$H NMR (400 MHz, $CDCl_3$) δ 11.48 (brs, 1H), 8.12 (dq, 1H, J=0.62, 4.77 Hz), 7.46 (dt, 1H, J=1.86, 6.4 Hz), 6.90 (s, 2H), 6.77 (m, 2H), 5.11 (s, 1H), 3.13 (s, 3H), 1.71 (s, 6H), 1.27 (s, 18H).

Elemental analysis for $C_{27}H_{35}N_3O_5$; Calc'd: C, 67.34; H, 7.33; N, 8.73; Found: C, 67.32; H, 7.22; N, 8.72.

The ability of the compounds of this invention to inhibit acyl-coenzyme A: cholesterol acyltransferase was established by initially showing that they inhibited intracellular cholesterol esterification by subjecting them to the standard experimental test procedure of Ross et al., J. Biol. Chem. 259 815 (1984).

Representative compounds were further tested in vivo to establish the percent inhibition of cholesterol absorption. In this study, normal rats were dosed (oral gavage) with $^{14}C$-cholesterol plus the test compound. Blood samples taken at six hours and/or intermittently up to twenty-four hours were analyzed and the percent inhibition of cholesterol absorption was calculated.

In addition, representative compounds were studied in vivo in cholesterol-cholic acid fed rats to determine the percent decrease of cholesterol in their plasma. This study involves rats which are, prior to testing, trained for one week to eat over a four hour time period each day. Upon initiation of the experiment, the rats diet is supplemented with 1.0 percent cholesterol and 0.25 percent cholic acid. The rats are dosed with the test compound by oral gavage just prior to adjust following the four hour feeding period. This is repeated for four days. On the fifth day, the rats are sacrificed and the total plasma cholesterol content is determined. The percent decrease in elevated plasma cholesterol levels is calculated in comparison with normal-fed controls.

TABLE 1

| Compound # | In Vitro % Inhibition (Conc., μM) | $IC_{50}$ (μM) |
|---|---|---|
| 1 | 65 (50) | — |
| 2 | 85 (50) | 0.9 |

TABLE 1-continued

| Compound # | In Vitro % Inhibition (Conc., μM) | $IC_{50}$ (μM) |
|---|---|---|
| 3 | 77 (50) | 0 |
| 4 | 99 (25) | 0.26 |
| 5 | 99 (25) | 1.1 |
| 6 | 99 (25) | 1.5 |
| 7 | 99 (25) | 0.83 |
| 8 | 85 (25) | 5.6 |
| 9 | 98 (25) | 5.6 |
| 10 | 97 (25) | 0.29 |
| 11 | 98 (25) | 2.8 |
| 12 | 96 (25) | −3.1 |
| 13 | 99 (25) | 0.19 |
| 14 | 99 (25) | 0.84 |
| 15 | 63 (50) | — |
| 16 | 84 (25) | 0.98 |
| 17 | 72 (25) | — |
| 18 | 60 (50) | — |
| 19 | 98 (25) | 2.4 |
| 20 | 96 (25) | 0.77 |
| 21 | 98 (25) | 0.25 |
| 22 | 93 (25) | 0.37 |
| 23 | 85 (25) | 3.5 |
| 24 | 96 (25) | 2.3 |
| 25 | 94 (25) | 0.5 |
| 26 | 92 (25) | 0.92 |
| 27 | 96 (25) | 0.23 |
| 28 | 98 (25) | 0.69 |
| 29 | 99 (25) | 0.23 |
| 30 | 42 (25) | — |
| 31 | 97 (25) | 0.91 |
| 32 | 98 (25) | 0.24 |
| 33 | 98 (25) | 0.38 |
| 34 | 98 (25) | 1.1 |
| 35 | 99 (25) | 0.54 |
| 36 | 99 (26) | 0.044 |
| 37 | 99 (25) | 0.69 |
| 38 | 99 (25) | 0.21 |
| 39 | 99 (25) | 0.37 |
| 40 | 99 (25) | 0.36 |
| 41 | 98 (25) | 0.26 |
| 42 | 98 (25) | 0.27 |
| 43 | 97 (25) | 0.41 |
| 44 | 82 (25) | 15 |
| 45 | 90 (25) | 5.2 |
| 46 | 98 (25) | 0.35 |
| 47 | 98 (25) | 0.26 |
| 48 | 94 (25) | 2.9 |
| 49 | 80 (25) | 4.5 |
| 50 | 74 (25) | — |
| 51 | 66 (25) | — |
| 52 | 89 (25) | 5.6 |
| 53 | 81 (25) | 5.2 |
| 54 | 98 (25) | 0.68 |
| 55 | 97 (25) | 3.0 |
| 56 | 97 (25) | 1.4 |
| 57 | 96 (25) | 0.41 |
| 58 | 99 (25) | 0.55 |
| 59 | 94 (25) | 0.7 |
| 60 | 99 (25) | 0.54 |
| 61 | 98 (25) | 0.16 |
| 62 | 99 (25) | 0.64 |
| 63 | 99 (25) | 0.09 |
| 64 | 99 (25) | 0.49 |
| 65 | 98 (25) | 2.3 |
| 66 | 98 (25) | 0.19 |
| 67 | 89 (50) | 4.5 |
| 68 | 98 (25) | 0.28 |
| 69 | 98 (25) | 2.8 |
| 70 | 24 (25) | — |
| 71 | 97 (25) | 0.53 |
| 72 | 98 (25) | 1.3 |
| 73 | 97 (25) | 1.3 |
| 74 | 97 | 0.29 |
| 76 | 96 (25) | 0.06 |
| 77 | 95 (25) | — |
| 79 | — | 0.24 |
| 81 | 90 (50) | |
| 82 | 94 (50) | |
| 83 | 86 (50) | |

TABLE 2

In Vivo Testing $^{14}$C-Cholesterol Absorption in Normal Rats

| Compound | Dose mg/kg | % Inhibition of Absorption |
|---|---|---|
| 2 | 200 | −88 |
| 48 | 200 | −84 |
| 59 | 200 | −21 |
| 4 | 200 | −93 |
| 5 | 200 | −91 |
| 21 | 75 | −83 |
| 27 | 20 | −58 |
| 32 | 20 | −79 |
| 33 | 50 | −86 |
| 37 | 50 | −85 |
| 40 | 10 | −69 |
| 43 | 10 | −52 |
| 46 | 10 | −82 |
| 47 | 10 | −83 |
| 8 | 10 | −16 |
| 52 | 10 | −29 |
| 53 | 10 | −50 |
| 81 | 3 | −90 |

TABLE 3

In Vivo Cholesterol-Cholic Acid Fed Rats

| Compound | Dose mg/kg | % Decrease in Plasma Cholesterol |
|---|---|---|
| 48 | 100 | −60 |
| 4 | 100 | −98 |
| 14 | 100 | −85 |
| 5 | 100 | −35 |
| 6 | 100 | −42 |
| 21 | 100 | −78 |
| 22 | 60 | −46 |
| 27 | 40 | −31 |
| 28 | 40 | −15 |
| 29 | 100 | −84 |
| 7 | 100 | 100 |
| 31 | 60 | −71 |
| 32 | 60 | 97 |
| 33 | 20 | −30 |
| 34 | 20 | −32 |
| 35 | 40 | −55 |
| 36 | 20 | −62 |
| 37 | 40 | −72 |
| 38 | 40 | −58 |
| 39 | 40 | −65 |
| 40 | 40 | −78 |
| 41 | 40 | −89 |
| 42 | 40 | −63 |
| 43 | 40 | −67 |
| 45 | 20 | −29 |
| 46 | 20 | −70 |
| 54 | 20 | −77 |
| 55 | 20 | −40 |

The effective doses at which a fifty percent reduction of plasma cholesterol was achieved were as follows:

TABLE 4

ED$_{50}$ for $^{14}$C-Cholesterol Absorption in Normal Fed Rats

| Compound | ED$_{50}$ (mg/kg) |
|---|---|
| 2 | 44 |
| 48 | 11 |
| 4 | 10 |
| 7 | 3 |
| 32 | 4 |
| 40 | 2 |
| 41 | 3 |
| 42 | 5 |
| 46 | 2 |
| 47 | 3 |

TABLE 5

ED$_{50}$ for Cholesterol-Cholic Acid Fed Rats

| Compound | ED$_{50}$ (mg/kg) |
|---|---|
| 2 | 99 |
| 48 | 25 |
| 4 | 64 |
| 14 | 16 |
| 7 | 6 |
| 32 | 17 |
| 37 | 18 |
| 40 | 7 |
| 41 | 7 |
| 46 | 8 |
| 47 | 16 |

From these data, the ability of the compounds to inhibit ACAT is clearly established. Hence, the compounds of this invention are useful in the treatment of those disease states which are amenable to treatment by reduction of the rate of cholesterol esterification, the rate of accumulation and deposits of cholesteryl esters on arterial walls and the rate of formation of atheromatous lesions. As such, the anti-atherosclerotic agents of this invention may be administered to a mammal in need of intracellular cholesteryl ester concentration reduction orally or parenterally in an amount sufficient to inhibit ACAT catalysis of cholesterol esterification.

In addition to ACAT inhibition, some of the compounds of this invention possess excellent antioxidant properties when examined in the manner disclosed by Parthasarathy et al., J. Clin. Invest., 77, 641 (1986) in low density lipoprotein oxidation studies and in the lipoperoxide study of Yagi, Biochemical Medicine, 15, 212 (1976). The products of Examples 75, 76, 77 and 79, supra, are demonstrated antioxidant properties in these standard procedures, representative of the other antioxidants of this invention. The use of antioxidants in the treatment of atherosclerosis is also known to be of therapeutic value.

The compounds of this invention may be administered by themselves or in combination with pharmaceutically acceptable liquid or solid carriers. Oral administration in conventional formulations as tablets, capsules, powders, or suspensions is preferred.

A solid carrier can include one or more substances which may also act as flavoring agents, lubricants, solubilisers, suspending agents, fillers, glidants, compression aids, binders or tablet-disintegrating agents; it can also be an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers are used in preparing solutions, suspensions, emulsions, syrups, elixirs and pressurized compositions. The active ingredient can be dissolved or suspended in a pharmaceutically acceptable liquid carrier such as water, an organic solvent, a mixture of both of pharmaceutically acceptable oils or fats. The liquid carrier can contain other suitable pharmaceutical additives such as solubilisers, emulsifiers, buffers, preservatives, sweeteners, flavoring agents, suspending agents, thickening agents, colors, viscosity regulators, stabilisers or osmo-regulators. Suitable examples of liquid carriers for oral and parenteral administration include water (particularly containing additives as above, e.g. cellulose derivatives, preferably sodium carboxymethyl cellulose solution), alcohols (including monohydric alcohols and polyhydric alcohols, e.g., glycols) and their derivatives, and oils (e.g. fractionated coconut oil and arachis oil). For parenteral administration, the carrier can also be an oil ester such as ethyl oleate and isopropyl myristate. Sterile liquid carriers are used in sterile liquid form compositions for parenteral administration. The liquid carrier for pressurized compositions can be halogenated hydrocarbon or other pharmaceutically acceptable propellent.

Liquid pharmaceutical compositions which are sterile solutions or suspensions can be utilized by, for example, intramuscular intraperitoneal or subcutaneous injection. Sterile solutions can also be administered intravenously. When the compound is orally active, it can be administered orally either in liquid or solid composition form.

Preferably, the pharmaceutical composition is in unit dosage form, e.g. as tablets or capsules. In such form, the composition is sub-divided in unit dose containing appropriate quantities of the active ingredient; the unit dosage forms can be packaged compositions, for example, packeted powders, vials, ampoules, prefilled syringes or sachets containing liquids. The unit dosage form can be, for example, a capsule or tablet itself, or it can be the appropriate number of any such compositions in package form.

The dosage to be used in the treatment of a specific hypercholesterolemic/atherosclerotic condition must be subjectively determined by the attending physician. The variables involved include the extent of the disease state, size, age and response pattern of the patient.

What is claimed is:

1.

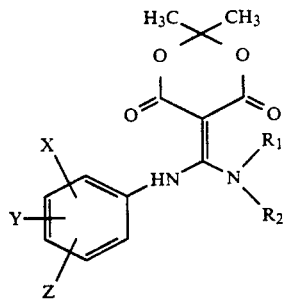

in which
X, Y and Z are, independently, hydrogen, halogen, hydroxy, nitro, cyano, carboxyl, trifluoromethyl, phenyl, amino, alkylamino of 1 to 6 carbon atoms, dialkylamino in which each alkyl group has 1 to 6 carbon atoms, alkyl of 1 to 6 carbon atoms, alkoxy of 1 to 6 carbon atoms or phenylalkyloxy of 7 to 9 carbon atoms;

R₁ is pyridinyl which can be substituted with one to three substituents selected from halogen, hydroxy, nitro, cyano, carboxyl, trifluoromethyl, phenyl, amino, alkylamino of 1 to 6 carbon atoms, dialkylamino in which each alkyl group has 1 to 6 carbon atoms, alkyl of 1 to 6 carbon atoms, or alkoxy of 1 to 6 carbon atoms; and R₂ is hydrogen, alkyl of 1 to 18 carbon atoms, cycloalkyl of 5 to 8 carbon atoms, phenyl, benzyl or substituted phenyl or benzyl in which said substituent is alkyl of 1 to 6 carbon atoms, alkoxy of 1 to 6 carbon atoms, halogen, cyano, trifluoromethyl, amino, nitro, alkylamino of 1 to 6 carbon atoms or dialkylamino of 1 to 6 carbon atoms;

or a pharmaceutically acceptable salt thereof.

2. A compound of claim 1 of the formula:

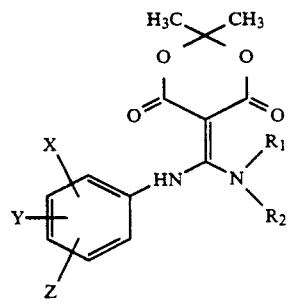

in which
X, Y and Z are, independently, alkyl of 1 to 6 carbon atoms, alkoxy of 1 to 6 carbon atoms, hydroxy, dialkylamino in which each alkyl group has from 1 to 6 carbon atoms or aralkoxy of 7 to 10 carbon atoms;

R₁ is pyridinyl; and

R₂ is hydrogen, alkyl of 1 to 18 carbon atoms, cycloalkyl of 5 to 8 carbon atoms, phenyl, benzyl or substituted phenyl or benzyl in which said substituent is alkyl of 1 to 6 carbon atoms, alkoxy of 1 to 6 carbon atoms, halogen, cyano, trifluoromethyl, amino, nitro, alkylamino of 1 to 6 carbon atoms or dialkylamino of 1 to 6 carbon atoms;

or a pharmaceutically acceptable salt thereof.

3. A compound of claim 1 which is 5-[(3,5-di-tert-butyl-4-hydroxy-phenylamino)-(pyridin-3-ylamino)-methylene-2,2-dimethyl-[1,3]dioxane-4,6-dione or a pharmaceutically acceptable salt thereof.

4. A compound of claim 1 which is 5-[(3,5-di-tert-butyl-4-hydroxy-phenylamino)-(pyridin-2-ylamino)-methylene-2,2-dimethyl-[1,3]dioxane-4,6-dione or a pharmaceutically acceptable salt thereof.

5. A compound of claim 1 which is 5-[(3,5-di-tert-butyl-4-hydroxy-phenylamino)-(pyridin-4-ylamino)-methylene-2,2-dimethyl-[1,3]dioxane-4,6-dione or a pharmaceutically acceptable salt thereof.

6. A compound of claim 1 which is 5-[(3,5-di-tert-butyl-4-hydroxy-phenylamino)-(methyl-pyridin-2-ylamino)-methylene]-2,2-dimethyl-[1,3]dioxane-4,6-dione or a pharmaceutically acceptable salt thereof.

* * * * *